(12) United States Patent  (10) Patent No.: US 9,042,006 B2
Armstrong  (45) Date of Patent: May 26, 2015

(54) SOLID STATE ILLUMINATION SOURCE AND INSPECTION SYSTEM

(71) Applicant: KLA-Tencor Corporation, Milpitas, CA (US)

(72) Inventor: J. Joseph Armstrong, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/022,190

(22) Filed: Sep. 9, 2013

(65) Prior Publication Data

US 2014/0071520 A1  Mar. 13, 2014

Related U.S. Application Data

(60) Provisional application No. 61/699,706, filed on Sep. 11, 2012.

(51) Int. Cl.
*H01S 3/10* (2006.01)
*H01S 3/109* (2006.01)
*H01S 3/23* (2006.01)
*H01S 3/30* (2006.01)
*G01N 21/95* (2006.01)
(Continued)

(52) U.S. Cl.
CPC . *H01S 3/10* (2013.01); *H01S 3/109* (2013.01); *H01S 3/06754* (2013.01); *H01S 3/094007* (2013.01); *H01S 3/2316* (2013.01); *H01S 3/302* (2013.01); *H01S 2301/02* (2013.01); *G01N 21/9501* (2013.01); *G01N 21/8806* (2013.01); *G01N 2021/95676* (2013.01)

(58) Field of Classification Search
CPC ................................. H01S 3/094; H01S 3/10
See application file for complete search history.

(56) References Cited

U.S. PATENT DOCUMENTS 4,178,561 A  12/1979  Hon et al.
5,144,630 A  9/1992  Lin
(Continued)

FOREIGN PATENT DOCUMENTS

CN  101702490 A  5/2010
DE  102007004235 B3  1/2008
(Continued)

OTHER PUBLICATIONS

International Search Report and Written Opinion dated Jul. 11, 2014 for PCT/US2014/030989, filed Mar. 18, 2014 in the name of KLA-Tencor Corporation.
(Continued)

*Primary Examiner* — Ari M Diacou
(74) *Attorney, Agent, or Firm* — Bever, Hoffman & Harms, LLP

(57) ABSTRACT

An exemplary illumination source for an inspection system includes a pulsed seed laser having a wavelength of approximately 1104 nm and a continuous wave, Raman seed laser having a wavelength of approximately 1160 nm. An optical coupler can combine outputs of the pulsed seed laser and the continuous wave, Raman seed laser. Pre-amplification stages can receive an output of the optical coupler. A power amplifier can receive an output of the pre-amplification stages. A sixth harmonic can be generated using the amplified, combined wavelength. Systems for inspecting a specimen such as a reticle, photomask or wafer can include one of the illumination sources described herein.

28 Claims, 25 Drawing Sheets

(51) Int. Cl.
*G01N 21/88* (2006.01)
*H01S 3/067* (2006.01)
*H01S 3/094* (2006.01)
*G01N 21/956* (2006.01)

(56) References Cited

U.S. PATENT DOCUMENTS

| | | | |
|---|---|---|---|
| 5,563,702 A | 10/1996 | Emery et al. | |
| 5,572,598 A | 11/1996 | Wihl et al. | |
| 5,742,626 A | 4/1998 | Mead et al. | |
| 5,825,562 A | 10/1998 | Lai et al. | |
| 5,999,310 A | 12/1999 | Shafer et al. | |
| 6,201,601 B1 | 3/2001 | Vaez-Iravani et al. | |
| 6,212,310 B1 * | 4/2001 | Waarts et al. | 385/24 |
| 6,249,371 B1 | 6/2001 | Masuda et al. | |
| 6,271,916 B1 | 8/2001 | Marxer et al. | |
| 6,498,801 B1 | 12/2002 | Dudelzak et al. | |
| 6,590,698 B1 * | 7/2003 | Ohtsuki et al. | 359/326 |
| 6,816,520 B1 | 11/2004 | Tulloch et al. | |
| 6,859,335 B1 | 2/2005 | Lai et al. | |
| 6,888,855 B1 | 5/2005 | Kopf | |
| 7,098,992 B2 * | 8/2006 | Ohtsuki et al. | 355/69 |
| 7,136,402 B1 | 11/2006 | Ohtsuki | |
| 7,339,961 B2 | 3/2008 | Tokuhisa et al. | |
| 7,352,457 B2 | 4/2008 | Kvamme et al. | |
| 7,463,657 B2 | 12/2008 | Spinelli et al. | |
| 7,471,705 B2 | 12/2008 | Gerstenberger et al. | |
| 7,525,649 B1 | 4/2009 | Leong et al. | |
| 7,528,943 B2 | 5/2009 | Brown et al. | |
| 7,593,437 B2 | 9/2009 | Staroudoumov et al. | |
| 7,593,440 B2 | 9/2009 | Spinelli et al. | |
| 7,623,557 B2 | 11/2009 | Tokuhisa et al. | |
| 7,627,007 B1 | 12/2009 | Armstrong et al. | |
| 7,643,529 B2 | 1/2010 | Brown et al. | |
| 7,715,459 B2 | 5/2010 | Brown et al. | |
| 7,813,406 B1 | 10/2010 | Nguyen et al. | |
| 7,822,092 B2 | 10/2010 | Ershov et al. | |
| 7,920,616 B2 | 4/2011 | Brown et al. | |
| 8,208,505 B2 | 6/2012 | Dantus et al. | |
| 8,298,335 B2 | 10/2012 | Armstrong | |
| 8,391,660 B2 | 3/2013 | Islam | |
| 8,503,068 B2 | 8/2013 | Sakuma | |
| 8,755,417 B1 * | 6/2014 | Dribinski | 372/22 |
| 2001/0000977 A1 | 5/2001 | Vaez-Iravani et al. | |
| 2002/0109110 A1 | 8/2002 | Some et al. | |
| 2002/0114553 A1 | 8/2002 | Mead et al. | |
| 2003/0161374 A1 | 8/2003 | Lokai | |
| 2004/0080741 A1 | 4/2004 | Marxer et al. | |
| 2005/0041702 A1 | 2/2005 | Fermann et al. | |
| 2005/0110988 A1 | 5/2005 | Nishiyama et al. | |
| 2005/0111081 A1 | 5/2005 | Shafer et al. | |
| 2005/0157382 A1 | 7/2005 | Kafka et al. | |
| 2005/0254065 A1 | 11/2005 | Stokowski | |
| 2006/0028984 A1 | 2/2006 | Wu et al. | |
| 2006/0171656 A1 | 8/2006 | Adachi et al. | |
| 2006/0239535 A1 | 10/2006 | Takada | |
| 2007/0002465 A1 | 1/2007 | Chuang et al. | |
| 2007/0146693 A1 | 6/2007 | Brown et al. | |
| 2007/0211773 A1 | 9/2007 | Gerstenberger et al. | |
| 2007/0263680 A1 | 11/2007 | Starodoumov et al. | |
| 2008/0186476 A1 | 8/2008 | Kusunose | |
| 2008/0204737 A1 | 8/2008 | Ogawa | |
| 2009/0084989 A1 | 4/2009 | Imai | |
| 2009/0180176 A1 | 7/2009 | Armstrong et al. | |
| 2009/0185583 A1 | 7/2009 | Kuksenkov et al. | |
| 2009/0185588 A1 * | 7/2009 | Munroe | 372/22 |
| 2009/0296755 A1 | 12/2009 | Brown et al. | |
| 2011/0062127 A1 | 3/2011 | Gu et al. | |
| 2011/0085149 A1 | 4/2011 | Nathan | |
| 2011/0134944 A1 | 6/2011 | Kaneda et al. | |
| 2011/0222565 A1 | 9/2011 | Horain et al. | |
| 2011/0228263 A1 | 9/2011 | Chuang et al. | |
| 2011/0279819 A1 | 11/2011 | Chuang et al. | |
| 2012/0033291 A1 | 2/2012 | Kneip | |
| 2012/0092657 A1 | 4/2012 | Shibata | |
| 2012/0113995 A1 | 5/2012 | Armstrong | |
| 2012/0120481 A1 | 5/2012 | Armstrong | |
| 2012/0137909 A1 | 6/2012 | Hawes et al. | |
| 2012/0314286 A1 | 12/2012 | Chuang et al. | |
| 2013/0021602 A1 | 1/2013 | Dribinski et al. | |
| 2013/0064259 A1 | 3/2013 | Wakabayashi et al. | |
| 2013/0077086 A1 * | 3/2013 | Chuang et al. | 356/51 |
| 2013/0088706 A1 | 4/2013 | Chuang et al. | |
| 2013/0313440 A1 | 11/2013 | Chuang et al. | |
| 2014/0111799 A1 | 4/2014 | Lee et al. | |
| 2014/0153596 A1 | 6/2014 | Chuang et al. | |
| 2014/0204963 A1 | 7/2014 | Chuang et al. | |

FOREIGN PATENT DOCUMENTS

| | | |
|---|---|---|
| EP | 0532927 A2 | 3/1993 |
| EP | 1194804 B1 | 7/2003 |
| EP | 2013951 A2 | 1/2009 |
| JP | 2002-258339 A | 9/2002 |
| JP | 2006-60162 A | 3/2006 |
| JP | 2007-206452 A | 8/2007 |
| JP | 2009-145791 A | 7/2009 |
| JP | 2010-54547 A | 3/2010 |
| JP | 2010-256784 A | 11/2010 |
| JP | 2011-23532 A | 2/2011 |
| JP | 2011-128330 A | 6/2011 |
| WO | WO03/069263 A2 | 8/2003 |
| WO | 2005/022705 A2 | 3/2005 |
| WO | 2009/082560 A2 | 7/2009 |
| WO | WO2010/037106 A2 | 4/2010 |
| WO | 2012/154468 A2 | 11/2012 |
| WO | 2013/015940 A2 | 1/2013 |

OTHER PUBLICATIONS

International Search Report and Written Opinion dated May 20, 2014 for PCT/US2014/016198, filed Feb. 13, 2014 in the name of KLA-Tencor Corporation.

International Search Report and Written Opinion dated May 13, 2014 for PCT/US2014/012902, filed Jan. 24, 2014 in the name of KLA-Tencor Corporation.

U.S. Appl. No. 11/735,967, filed Apr. 16, 2007 by Vladimir L. Dribinski et al.

Dianov et al., "Bi-doped fiber lasers: new type of high-power radiation sources" Conference on Lasers and Electro-Optics, May 6-11, 2007, 2 pages.

Kalita et al., "Multi-watts narrow-linewidth all fiber Yb-doped laser operating at 1179 nm", Optics Express, 18 (6), pp. 5920-5925 (2010).

Kashiwagi et al., "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).

Mead et al. "Solid-state lasers for 193-nm photolithography", Proc. SPIE 3051, Optical Microlithography X, pp. 882-889 (Jul. 7, 1997).

Saikawa et al. "52 mJ narrow-bandwidth degenerated optical parametric system with a large-aperture periodically poled MgO:LiNbO3 device", Optics Letters, 31 (#21), 3149-3151 (2006).

Sakuma et al. "High power, narrowband, Duv laser source by frequency mixing in CLBO", Advanced High-Power Lasers and Applications, Nov. 2000, pp. 7-14, Ushio Inc.

Sakuma et al., "True CW 193.4-nm light generation based on frequency conversion of fiber amplifiers", Optics Express 19 (16), 15020-15025 (2011).

Sasaki et al. "Progress in the growth of a CsLiB6O10 crystal and its application to ultraviolet light generation", Optical Materials, vol. 23, 343-351 (2003).

Shirakawa et al., "High-power Yb-doped photonic bandgap fiber amplifier at 1150-1200nm", Optics Express 17 (2), 447-454 (2009).

Ter-Mikirtychev et al., "Tunable LiF:F2—color center laser with an intracavity integrated-optic output coupler", Journal of Lightwave Technology, 14 (10), 2353-2355 (1996).

Yoo et al., "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.

(56) References Cited

OTHER PUBLICATIONS

Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.

* cited by examiner

SOLID STATE ILLUMINATION SOURCE AND INSPECTION SYSTEM

RELATED APPLICATIONS

The present application claims priority to U.S. Provisional Patent Application 61/699,706, entitled, "Solid-State Laser and Inspection System Using 193 nm Laser" and filed Sep. 11, 2012, which is incorporated by reference herein.

The present application is related to U.S. Provisional Application 61/538,353, entitled "Solid-State 193 nm Laser And An Inspection System Using A Solid-State 193 nm Laser" and filed Sep. 23, 2011, U.S. Provisional Application 61/559,292, filed Nov. 11, 2011, entitled "Solid State 193 nm Laser And An Inspection System Using A Solid-State 193 nm Laser", U.S. Provisional Application 61/591,384, entitled "Solid-State 193 nm Laser And An Inspection System Using A Solid-State 193 nm Laser" and filed Jan. 27, 2012, U.S. Provisional Application 61/603, 911, entitled "Solid-State 193 nm Laser And An Inspection System Using A Solid-State 193 nm Laser" and filed Feb. 27, 2012, and co-pending U.S. patent application Ser. No. 13/558,318, entitled "Solid-State 193 nm Laser And An Inspection System Using A Solid-State 193 nm Laser" by Chuang et al. and filed Jul. 25, 2012. All of the aforementioned applications are incorporated by reference herein.

The present application is also related to U.S. patent application Ser. No. 11/735,967, entitled "Coherent light generation below about 200 nm" and filed Apr. 16, 2007, which is incorporated by reference herein.

BACKGROUND OF THE DISCLOSURE

1. Field of the Disclosure

The present application relates to a solid state laser that generates deep-UV light (such as near 193 nm in wavelength) by harmonic conversion of an infra-red fundamental wavelength. Such a laser is suitable for use in photomask, reticle, or wafer inspection.

2. Related Art

Shorter wavelength laser light can produce higher resolution images, which in a laser inspection system can provide better information regarding features and defects on the imaged samples. To meet the increasing demand for laser inspection systems having ever higher resolution, the current trend in the semiconductor industry is toward the development of short wavelength UV-DUV laser inspection systems (i.e. systems utilizing laser light below 250 nm). For example, short-wavelength UV-DUV laser inspections systems operating with 213 nm, 206 nm, or 193 nm laser light are currently being developed.

To minimize the cost and complexity required to generate an optical system for a short wavelength UV-DUV laser inspection system, an illumination source must be able to generate laser light in which substantially all of the light energy is within a narrow bandwidth. In UV-DUV laser inspection systems, the bandwidth range at which 95% of the energy is contained (i.e. the light's "E95" bandwidth value) is generally the desired goal. Therefore, the challenge is to provide an illumination source that generates narrow band UV laser light that is both short wavelength UV-DUV (e.g. light having a nominal wavelength value below 250 nm) and has a narrow E95 bandwidth (i.e. within ±1%, and preferably within ±0.1%, of the nominal or "central" UV frequency).

There are two types of solid state lasers typically used in the generation of narrow band UV light: bulk lasers and fiber lasers. Bulk lasers include an active solid medium of glass or another crystalline material that is doped with rare earth elements, such as neodymium, chromium, erbium, or ytterbium. Bulk lasers can produce laser light having very narrow bandwidths and high peak power, which allows for the use of less complex (and therefore lower cost) optical systems. However, the wavelength choices for bulk lasers are very limited and thus are not suitable for some laser inspection systems. Moreover, generating reliable high power light from a bulk laser is challenging.

In contrast to bulk lasers, fiber lasers include an active gain medium formed by an optical fiber doped with rare-earth elements, such as erbium, ytterbium, neodymium, dysprosium, holmium, praseodymium, or thulium. Fiber lasers are an attractive choice for generating fundamental light in laser inspection systems because they can generate laser light having high peak power. Moreover, the frequency of the laser light can be "tuned" to a specified frequency by altering the amounts of doping materials in the fiber(s).

FIG. 1 illustrates a conventional fiber-based illumination source 100, which can generate UV laser light for an inspection system. Fiber-based illumination source 100 has a master oscillator power amplifier (MOPA) configuration that includes a seed laser 101 and a fiber amplifier 105 to boost the output power. Although a MOPA configuration is more complex than a bulk laser that can directly generate the required output wavelength and power, its constituent components are generally off the shelf and therefore may be simpler to develop than a new bulk laser with higher output power.

For example, in this embodiment, fiber-based illumination source 100 includes a seed laser 101 that outputs pulsed light, e.g. at 1060 nm. An optical isolator 102 receives the pulsed light output and ensures that its transmission is in only one direction. Specifically, optical isolator 102 uses a Faraday rotator and its associated polarization to prevent unwanted feedback. An optical coupler 103 receives the polarized output of optical isolator 102 as well an input from a pumping light source 104. Pumping light source 104 is used to transfer energy into the gain medium of fiber amplifier 105. This energy is absorbed by the medium, thereby exciting states in its atoms. In typical embodiments, the pump energy can be provided by an electric current or light. However, in either embodiment, the pump power is higher than the lasing threshold of seed laser 101.

A fiber amplifier 105 receives the output of optical coupler 103 and provides power amplification to the energized, pulsed light. In one embodiment, fiber amplifier 105 includes one or more ytterbium-doped fibers (YbDFs). An optical isolator 106 can receive the amplified, pulsed light and eliminate feedback, as described above. Note that a MOPA configuration can be sensitive to back-reflection, particularly after light amplification. Therefore, optical isolators (e.g. optical isolators 102 and 106) can include a Faraday isolator to mitigate this feedback sensitivity. An optical filter 107 can receive the polarized output of optical isolator 106 and generate an output light 108. In one embodiment, output light 108 can include one or more wavelength components (i.e. fundamental light sources). When multiple wavelength components are present, additional components, such as switches, can be used to select the desired wavelength component. In one embodiment, additional amplification stages including optical isolators, pumping light sources, optical couplers, fiber amplifiers, and optical filters can be included in fiber-based illumination source 100.

Unfortunately, each additional amplification stage adds complexity, especially at high average and peak powers. At average power levels of 40 W and peak powers of 20 kW it is very difficult to splice optical fibers so they will not damage.

In addition, active cooling of the fibers and connectors becomes necessary. High power amplifiers also require increased pump powers adding to the heat generation. Pulsed sources also cause self-phase modulation (SPM) which will increase the spectral bandwidth of the laser. This places fundamental limits on how much average and peak power can be extracted from a fiber amplifier. Therefore, a need arises for an improved illumination source.

SUMMARY OF THE DISCLOSURE

An illumination source for an inspection system is described herein. This illumination source includes a pulsed seed laser having a wavelength of approximately 1104 nm and a continuous wave, Raman seed laser having a wavelength of approximately 1160 nm. An optical coupler can combine outputs of the pulsed seed laser and the continuous wave, Raman seed laser. Pre-amplification stages can receive an output of the optical coupler. A power amplifier can receive an output of the pre-amplification stages.

Another illumination source for an inspection system is described herein. This illumination source includes a pulsed seed laser with a wavelength of approximately 1104 nm and pre-amplification stages for receiving an output of the pulsed seed laser. An optical coupler can combine an output of the pre-amplification stages and that of a continuous wave, Raman seed laser having a wavelength of approximately 1160 nm. A power amplifier can receive an output of the optical coupler.

Yet another illumination source for an inspection system is described herein. This illumination source includes a pulsed seed laser with a wavelength of approximately 1104 nm and pre-amplification stages for receiving an output of the pulsed seed laser. A power amplifier can amplify an output of the pre-amplification stages. An optical coupler can combine outputs of the power amplifier and a continuous wave, Raman seed laser having a wavelength of approximately 1160 nm. A Raman gain fiber can receive an output of the optical coupler.

The pre-amplification stages can include a plurality of sequentially-connected pre-amplifiers. In one embodiment, at least one pre-amplifier uses pumped light in a direction of propagation of an input light. For example, at least one pre-amplifier can include an ASE filter for receiving an input from an upstream component of the illumination source, a pump laser, an optical coupler for combining outputs of the ASE filter and the pump laser, and a fiber amplifier for amplifying an output of the optical coupler. In another embodiment, at least one pre-amplifier uses pumped light in a direction opposite to propagation of an input light. For example, at least one pre-amplifier can include an ASE filter for receiving an input from an upstream component of the illumination source, a fiber amplifier for amplifying an output of the ASE filter, a pump laser, and an optical coupler for combining outputs of the fiber amplifier and the pump laser. In yet another embodiment, at least one pre-amplifier uses pumped light in a first direction opposite to propagation of an input light as well as in a second direction of the propagation. For example, at least one pre-amplifier can include an ASE filter for receiving an input from an upstream component of the illumination source, a first pump laser, a first optical coupler for combining outputs of the ASE filter and the first pump laser, a fiber amplifier for amplifying an output of the first optical coupler, a second pump laser, and a second optical coupler for combining outputs of the fiber amplifier and the second pump laser.

A method of generating laser light of a deep UV wavelength of approximately 193 nm is described. In this method, a first wavelength of approximately 1104 nm is generated, the first wavelength being generated by a pulsed seed laser. A second wavelength of approximately 1160 nm is generated, the second wavelength being generated by a Raman seed laser. The first wavelength and the second wavelength are combined to generate a combined wavelength. The combined wavelength is amplified. A sixth harmonic of the combined wavelength can be generated to provide the approximately 193 nm.

Another method of generating laser light of a deep UV wavelength of approximately 193 nm is described. In this method, a first wavelength of approximately 1104 nm can be generated, the first wavelength being generated by a pulsed seed laser. The first wavelength is amplified to generate a first amplified wavelength. A second wavelength of approximately 1160 nm is generated, the second wavelength being generated by a Raman seed laser. The first amplified wavelength and the second wavelength can be combined to generate a combined wavelength. The combined wavelength can be amplified to generate a second amplified wavelength. A sixth harmonic of the second amplified wavelength can be generated to provide the approximately 193 nm.

Yet another method of generating laser light of a deep UV wavelength of approximately 193 nm is described. In this method, a first wavelength of approximately 1104 nm is generated, the first wavelength being generated by a pulsed seed laser. The first wavelength is amplified to generate a first amplified wavelength. A second wavelength of approximately 1160 nm is generated, the second wavelength being generated by a Raman seed laser. The first amplified wavelength and the second wavelength can be combined to generate a combined wavelength. The combined wavelength can be amplified using a Raman gain fiber to generate a second amplified wavelength. A sixth harmonic of the second amplified wavelength can be generated to provide the approximately 193 nm.

Systems for inspecting a specimen such as a reticle, photomask or wafer are also described herein. These systems can include one of the illumination sources described herein.

DETAILED DESCRIPTION OF THE DRAWINGS

Figure 1:
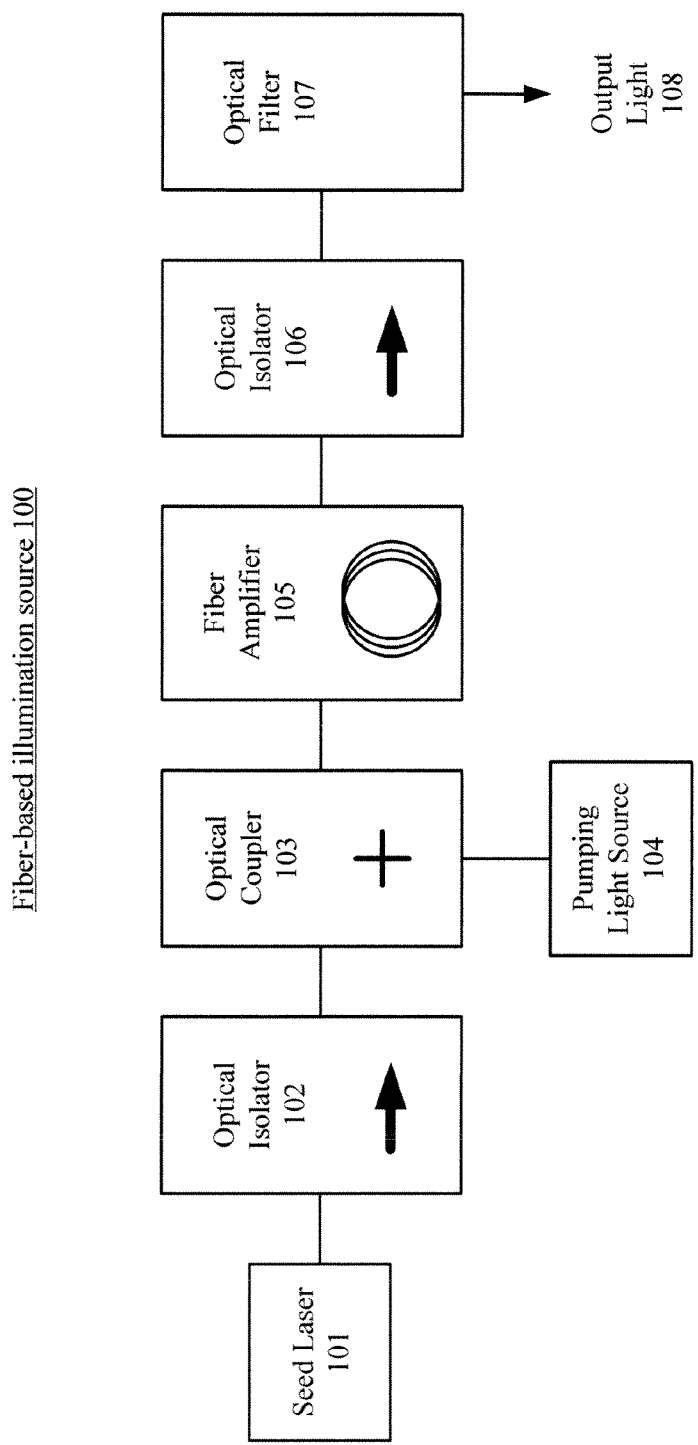
FIG. 1 illustrates a conventional fiber-based illumination source, which can generate UV laser light for an inspection system.
Figure 2A:
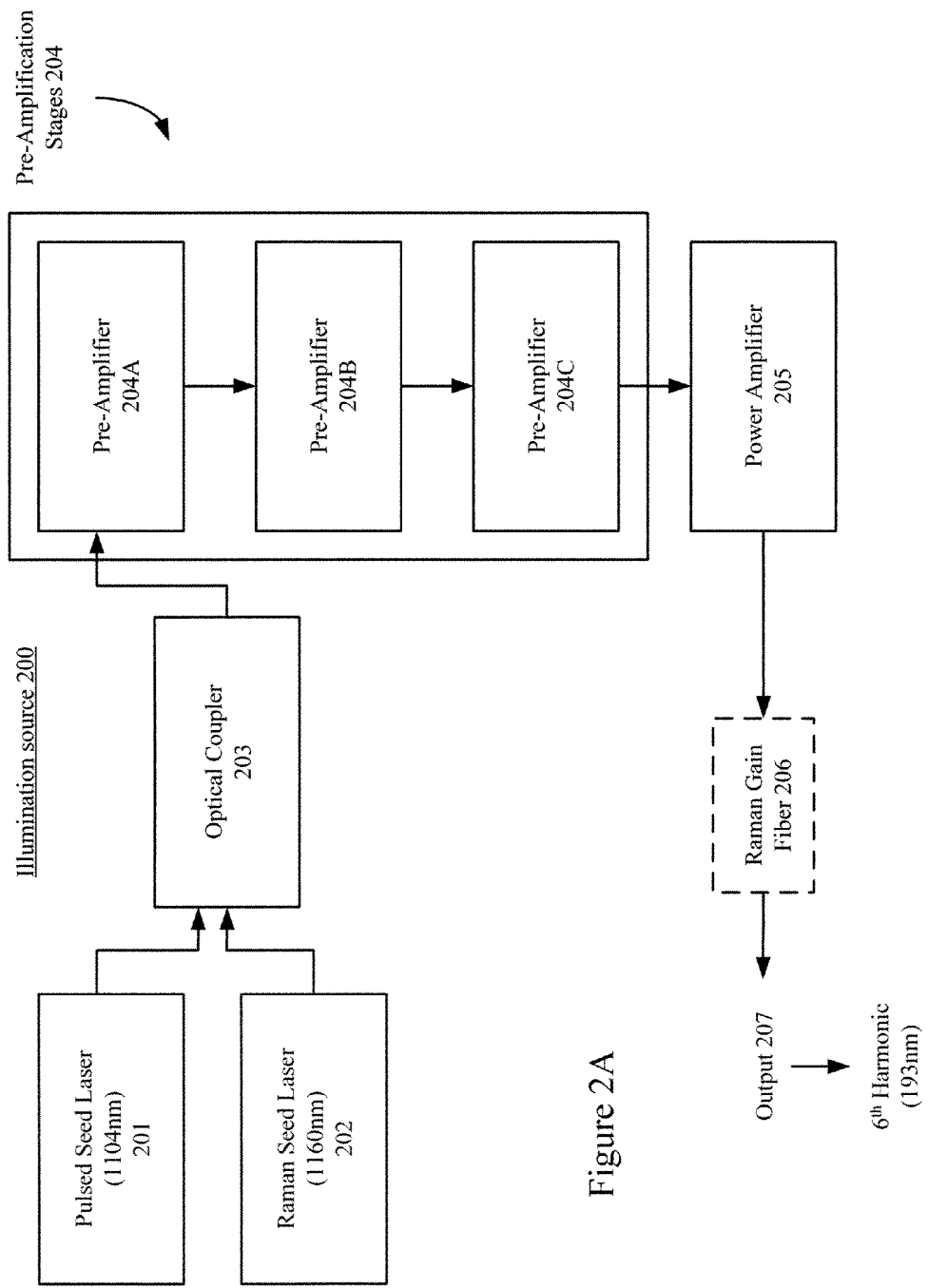
FIG. 2A illustrates a block diagram of a fiber-based illumination source, which can generate UV laser light for an inspection system. The illumination source includes a Raman seed laser having 1160 nm wavelength and a pulsed seed laser having 1104 nm wavelength, which are combined before a plurality of sequentially-connected pre-amplification stages and a downstream power amplifier.

FIG. 2A illustrates a block diagram of a fiber-based illumination source 200, which can generate UV laser light for an inspection system. Illumination source 200 includes a pulsed seed laser 201 having a wavelength of approximately 1104 nm and a Raman seed laser 202 having a wavelength of substantially 1160 nm (i.e. the separation of the two wavelengths corresponds substantially to the peak of a Raman transition in fused silica). The pulsed seed of pulsed seed laser 201 and the Raman seed of Raman seed laser 202 are optically combined in an optical coupler 203. The output of optical coupler 203 is then provided to a plurality of sequentially-coupled pre-amplification stages 204. The output of pre-amplification stages 204 is in turn provided to a power amplifier 205. In the embodiment shown in FIG. 2A, pre-amplification stages 204 include three pre-amplifiers 204A, 204B, and 204C. However, other embodiments of illumination source 200 can include any number of pre-amplifiers depending on the desired output power levels.

Figure 5A:
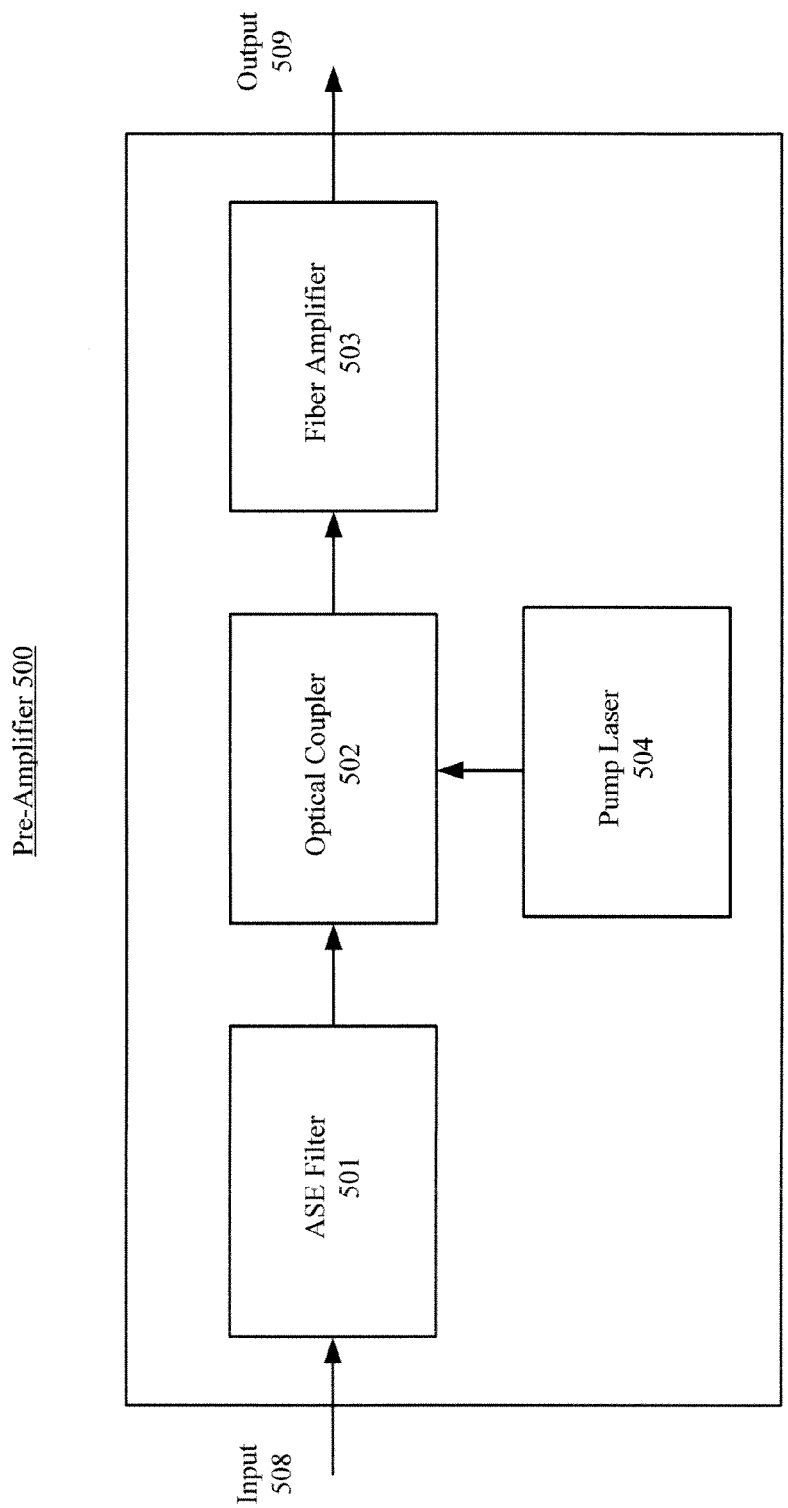
FIG. 5A illustrates a block diagram of an exemplary pre-amplifier that can be used in the fiber-based illumination sources of FIGS. 2A, 3A, and 4A.
Figure 5B:
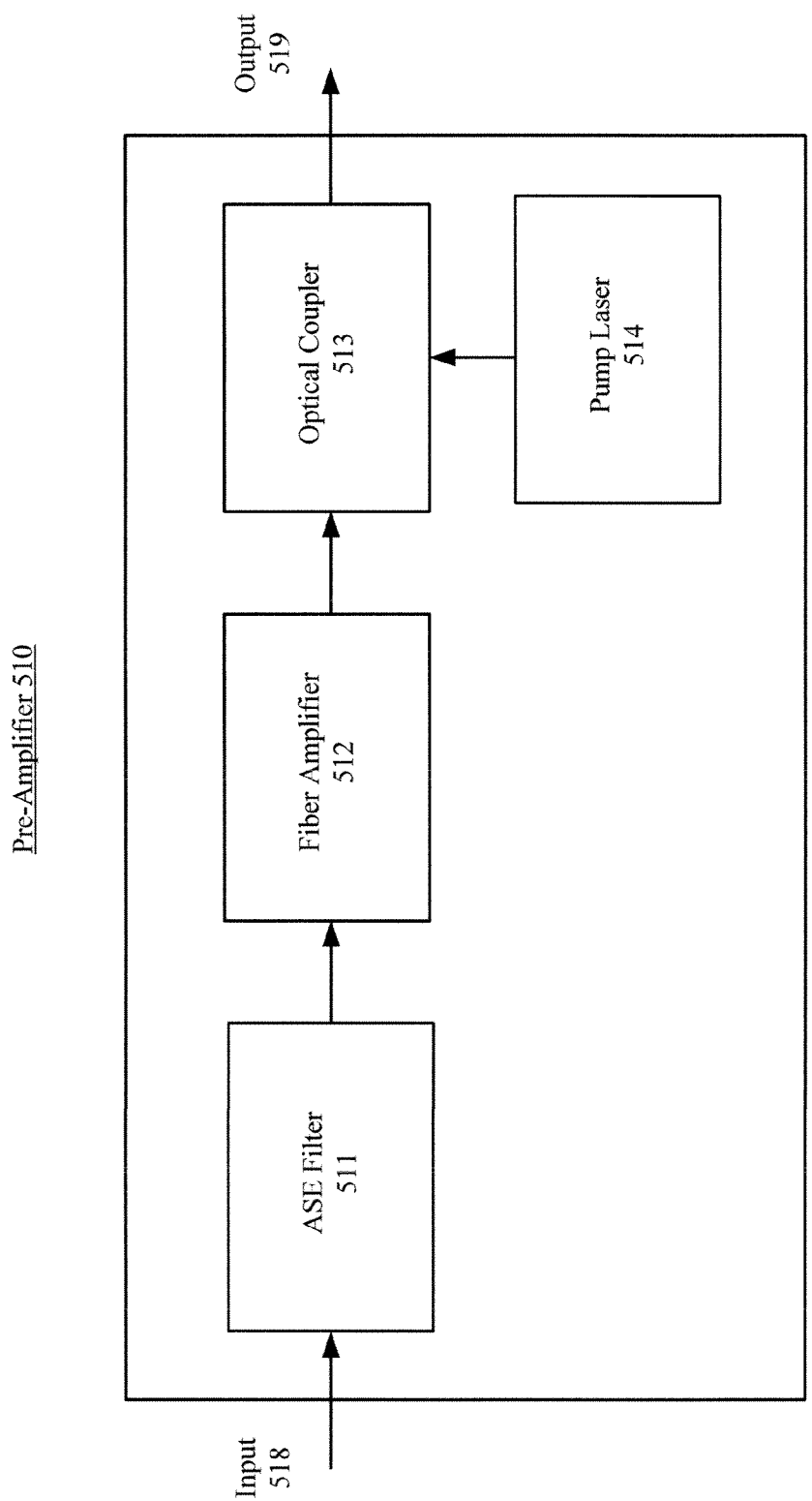
FIG. 5B illustrates a block diagram of another exemplary pre-amplifier that can be used in the fiber-based illumination sources of FIGS. 2A, 3A, and 4A.
Figure 6:
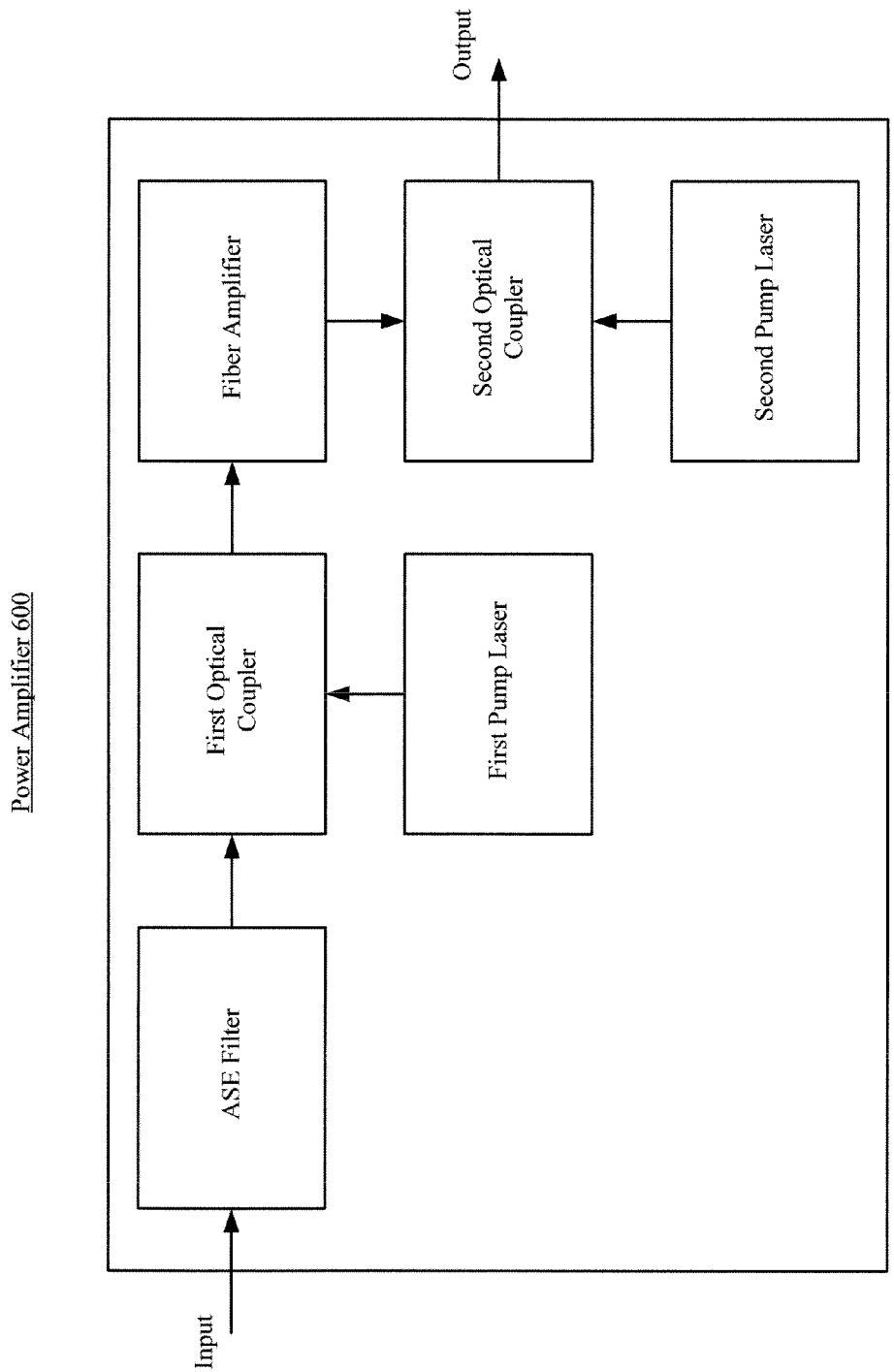
FIG. 6 illustrates a block diagram of an exemplary power amplifier that can be used in the fiber-based illumination sources of FIGS. 2A, 3A, and 4A.

In one embodiment, the wavelength of 1104 nm is chosen for pulsed seed laser 201 because it will most efficiently pump the Raman gain at 1160 nm (exemplary pumping is described in reference to FIGS. 5A, 5B, and 6). However, because the Raman gain in fused silica (which may be used in one or more of the Raman gain fiber 206, the pre-amplification stages 204 and the power amplifier 205) is very broad (over 60 nm), it is possible to pump the 1160 nm Raman conversion with a wide range of wavelengths. Note that pulsed seed laser 201 can have a variety of pulse widths, repetition rates, peak powers, and pulse shapes. Pulsed seed laser 201 can be a mode-locked laser, a Q-switched laser, a gain-switched laser, or a diode laser. It is also possible to use a continuous wave laser, whose output is then chopped using an electro optic modulator. The use of a continuous wave laser facilitates easy adjustment of the repetition rate, the pulse width, and/or the pulse shape. For example, the Raman generation is very efficient with a square pulse shape.

The use of a Raman seed laser is of particular import in the illumination sources described herein. Specifically, a Raman seed laser is optically pumped, but does not produce a population inversion as in conventional lasers. Instead, in a Raman seed laser, photons are absorbed and remitted as lower frequency photons by stimulated Raman scattering. The difference between the two photon energies can be fixed to correspond to the gain medium of the fiber amplifiers used in the illumination source. This correspondence allows a specific laser output wavelength to be generated based on a judiciously-chosen pump laser wavelength (e.g. the wavelength described above).

In one preferred embodiment, the Raman seed of Raman seed laser 202 has a wavelength of substantially 1160.2 nm so its $6^{th}$ harmonic will be at substantially 193.4 nm. However it is possible to use different wavelengths and still be within the scope of this invention. In one preferred embodiment, Raman seed laser 202 is a continuous wave laser with a very narrow bandwidth to ensure that the bandwidth of the stimulated Raman scattering in optical coupler 203 is as narrow as possible. In other embodiments, Raman seed laser 202 can be a pulsed source synchronized with pulsed seed laser 201. In some embodiments, spectral filters (described below) can be positioned in pre-amplifier stages 204 to prevent any undesirable emissions from damaging either pulsed seed laser 201 or Raman seed laser 202. Exemplary Raman seed lasers can be implemented using Raman fiber lasers or with silicon Raman lasers. The configuration of illumination source 200 can advantageously couple the Raman seed of Raman seed laser 202 and the pulsed seed of pulsed seed laser 201 into pre-amplification stages 204 at low power levels so there is low stress on components downstream of power amplifier 205 (e.g. a fused combiner following output 207). Otherwise, optical combiners and fiber splices are difficult to accomplish with long lifetimes with high average and high peak powers. As an example, reliability begins to be a problem with 40 W of average power, and 20 kW of peak power in a 100 MHz pulsed laser. Notably, the sixth harmonic of output 207, which is approximately 193 nm, e.g. 193.4 nm, can be generated from output 207. Note that the $6^{th}$ harmonic of 1104 nm is 184 nm, which is not the correct wavelength for many desired application.

In some embodiments, Raman seed laser 202 provides a wavelength at substantially 1160 nm; however, the majority of the Raman gain can come from Raman gain amplifier 206, not pre-amplification stages 204 and power amplifier 205. In other embodiments, the pre-amplifiers of pre-amplification stages 204 are designed so that the fiber amplifiers therein (described below in reference to FIGS. 5A and 5B) can produce the desired Raman gain output in the fiber amplifiers. In one embodiment, an auxiliary Raman gain fiber 206, positioned to receive an output of power amplifier 205, can provide a portion of the Raman gain without amplifying the pump wavelength. Such a configuration can facilitate tailoring the Raman gain independent of the amplifier gains provided by pre-amplification stages 204 and power amplifier 205.

Figure 2B:
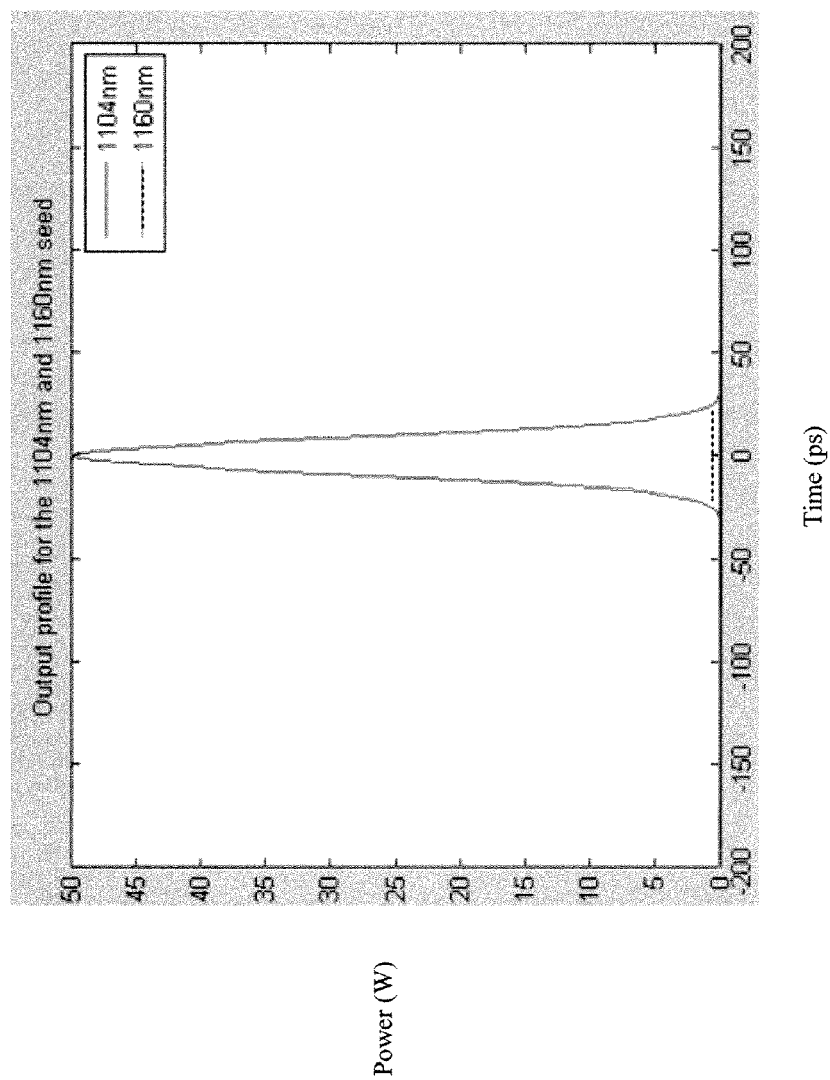
FIGS. 2B and 2C illustrate waveforms at two points in the illumination source of FIG. 2A.
Figure 2C:
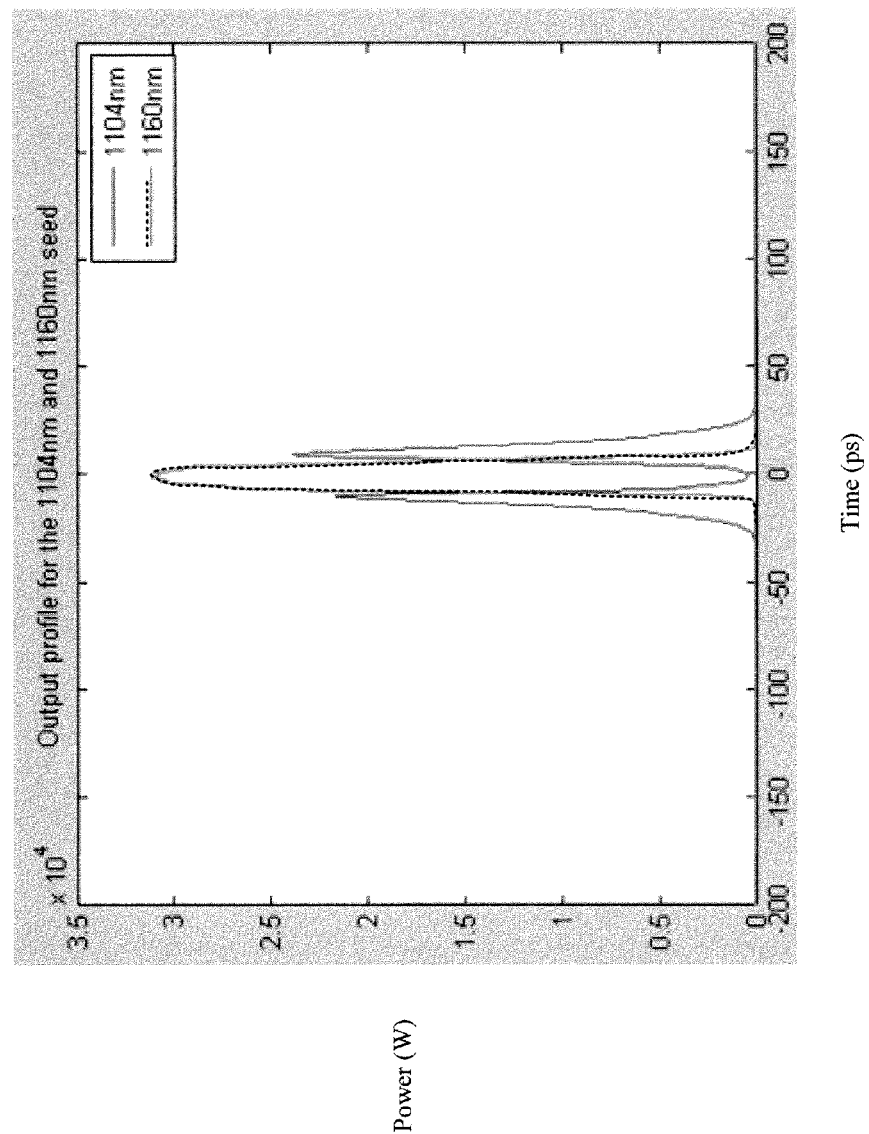

FIG. 2B shows an example of the seed profiles at the input to pre-amplification stages 204. In this example, pulsed source 1104 nm has a 20 ps pulse width (full width half maximum FWHM) and 50 W of peak power. The 1160 nm seed laser is a continuous laser with an average power of 100 mW. It is also possible to use pulses that are much longer, such as those that arise from a chopped CW laser, or much shorter such as those from a femtosecond laser. FIG. 2C shows the temporal profiles of the 1104 nm light and the 1160 nm light at the output of power amplifier 205. As can be seen, a significant portion of the 1104 nm light has been changed to 1160 nm light through the Raman process. Additional Raman gain is possible by adding an un-doped portion to Raman gain fiber 206.

Figure 3A:
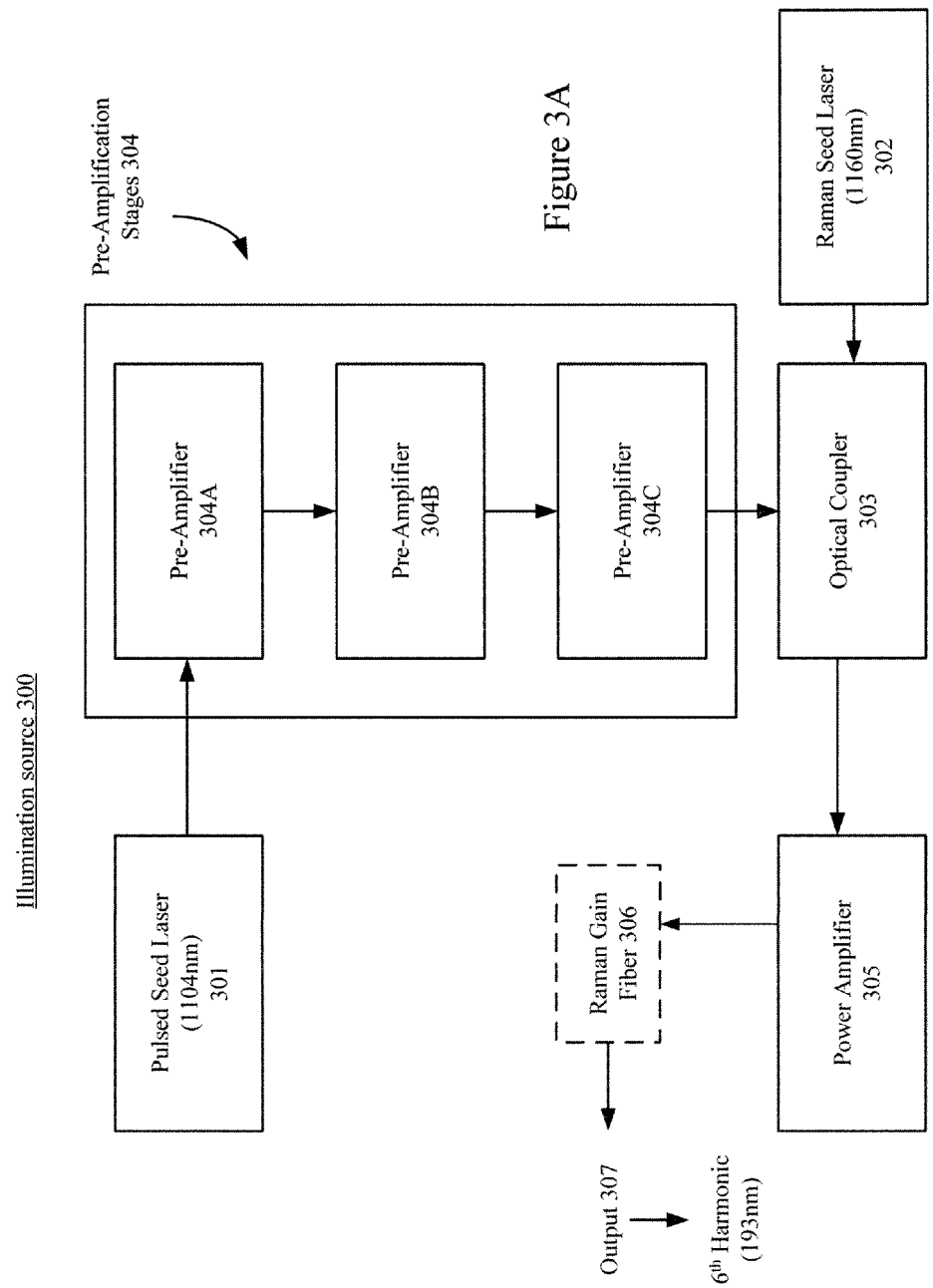
FIG. 3A illustrates a block diagram of another fiber-based illumination source, which can generate UV laser light for an inspection system. The illumination source includes a pulsed seed laser having 1104 nm wavelength provided to a plurality of sequentially-connected pre-amplification stages, and a Raman seed laser having 1160 nm wavelength injected into the downstream power amplifier.

FIG. 3A illustrates a block diagram of another fiber-based illumination source 300, which can generate UV laser light for an inspection system. Illumination source 300 includes a pulsed seed laser 301 having a wavelength of approximately 1104 nm, which can provide its output to a plurality of sequentially-coupled pre-amplification stages 304. In the embodiment shown in FIG. 3A, pre-amplification stages 304 include three pre-amplifiers 304A, 304B, and 304C. However, other embodiments of illumination source 300 can include any number of pre-amplifiers depending on the desired output power levels. The output of pre-amplification stages 304 and an output of a Raman seed laser 302 are provided to an optical coupler 303, which in turn provides its output to a power amplifier 305.

In one embodiment, the wavelength of 1104 nm is chosen for pulsed seed laser 301 because it will most efficiently pump the Raman gain at 1160 nm. However, because the Raman gain in fused silica (which may be used in one or more of the Raman gain fiber 306, the pre-amplification stages 304 and the power amplifier 305) is very broad (over 60 nm), it is possible to pump the 1160 nm Raman conversion (e.g. the Raman process performed by pre-amplification stages 304, power amplifier 305, and/or Raman gain fiber 306) with a wide range of wavelengths. Note that pulsed seed laser 301 can have a variety of pulse widths, repetition rates, peak powers, and pulse shapes. Pulsed seed laser 201 can be a mode-locked laser, a Q-switched laser, a gain-switched laser, or a diode laser. It is also possible to use a continuous wave laser, whose output is then chopped using an electro optic modulator. The use of a continuous wave laser facilitates easy adjustment of the repetition rate, the pulse width, and/or the pulse shape. For example, the combination of an amplified square pulse shape from pre-amplification stages 304 with the Raman seed from Raman seed laser 302 is very efficient.

In one preferred embodiment, the seed of Raman seed laser 202 has a wavelength of substantially 1160.2 nm so its $6^{th}$ harmonic will be at substantially 193.4 nm. However it is possible to use different wavelengths and still be within the scope of this invention. In one preferred embodiment, Raman seed laser 302 is a continuous wave laser with a very narrow bandwidth to ensure that the bandwidth of the stimulated Raman scattering in optical coupler 303 is as narrow as possible. In other embodiments, Raman seed laser 302 can be a pulsed source synchronized with pulsed seed laser 301.

The configuration of illumination source 300 can advantageously allow the Raman seed of Raman seed laser 302 to be injected at low powers, thereby avoiding losses associated with any internal filters of power amplifier 305 (described in reference to FIG. 6). Moreover, this low power injection ensures low stress on components downstream of power amplifier 305 (e.g. a fused combiner following output 307). Notably, the sixth harmonic of output 307, which is approximately 193 nm, can be generated from output 307.

In one embodiment, power amplifier 305 can include an amplifier fiber that produces the desired 1160 nm output from the Raman gain generated by pre-amplification stages 304. In one optional embodiment, a Raman gain fiber 306 can receive the output of power amplifier 305 to perform a portion of the Raman gain without amplifying the pump wavelength (the wavelength of pulsed seed laser 301). In this embodiment, the Raman gain can be tailored independently of the amplifier gain of the power amplifier 305.

Figure 3B:
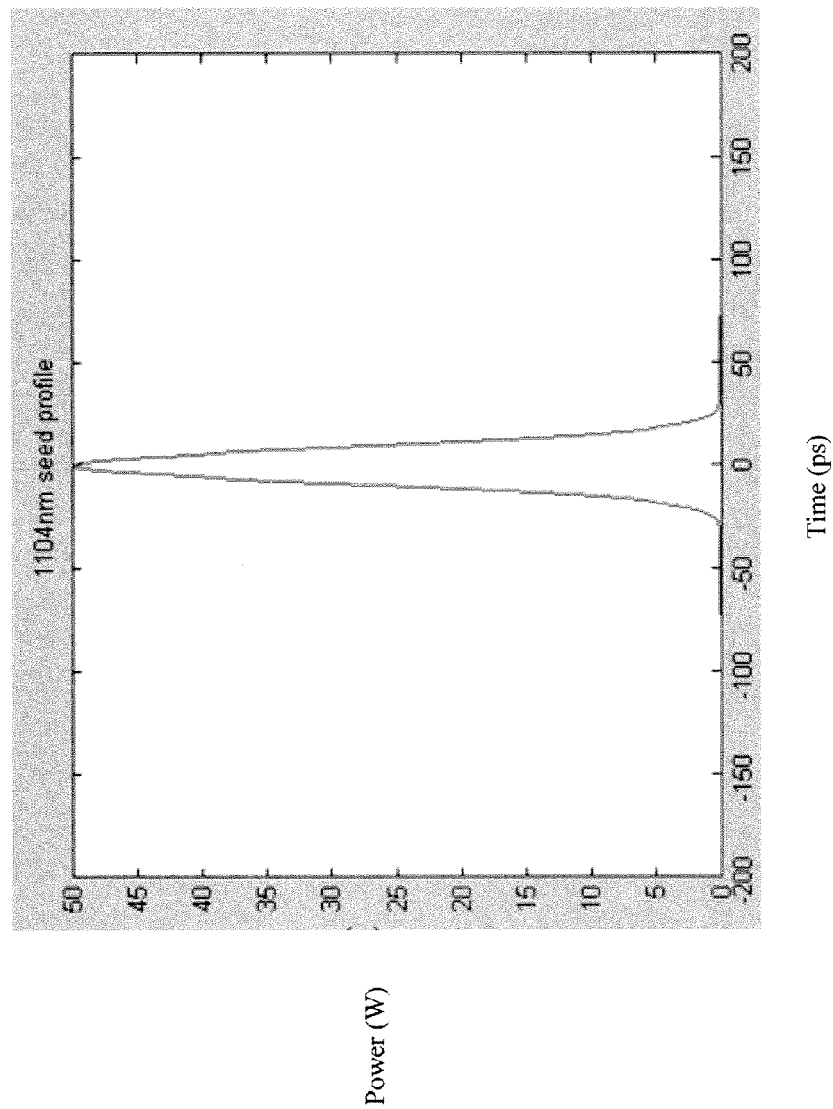
FIGS. 3B, 3C, and 3D illustrate waveforms at three points in the illumination source of FIG. 3A.
Figure 3C:
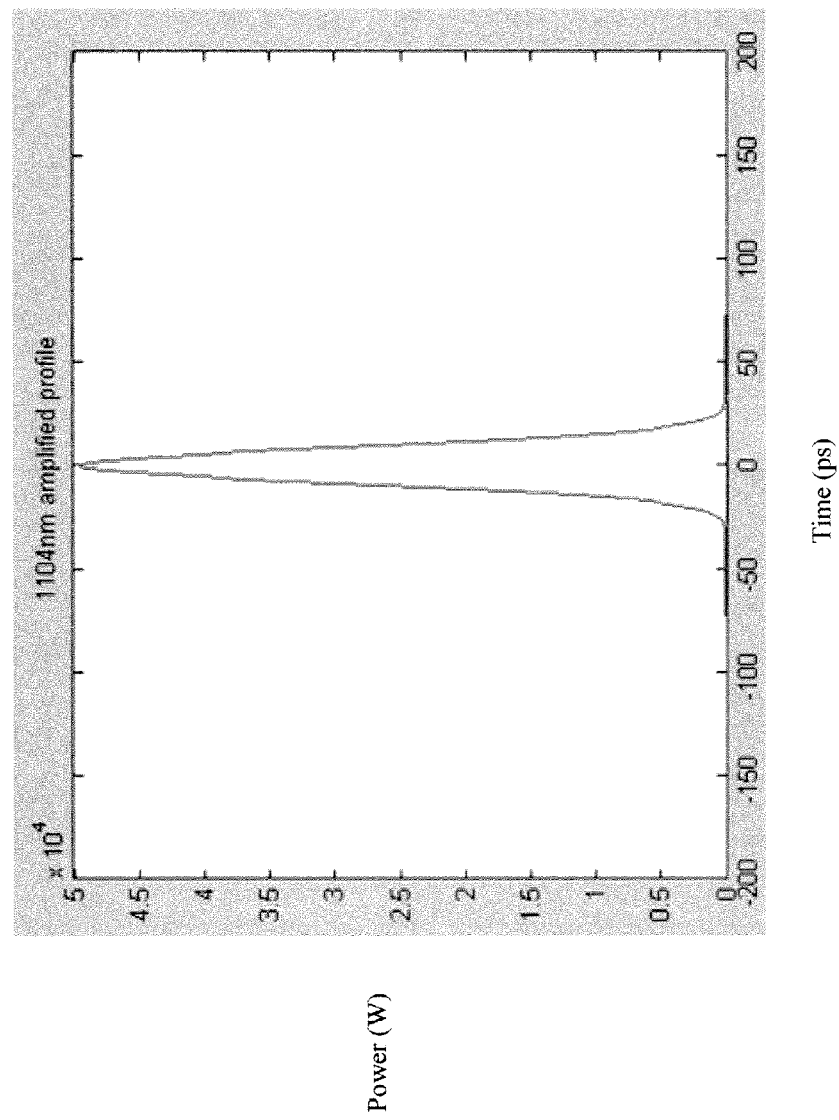
Figure 3D:
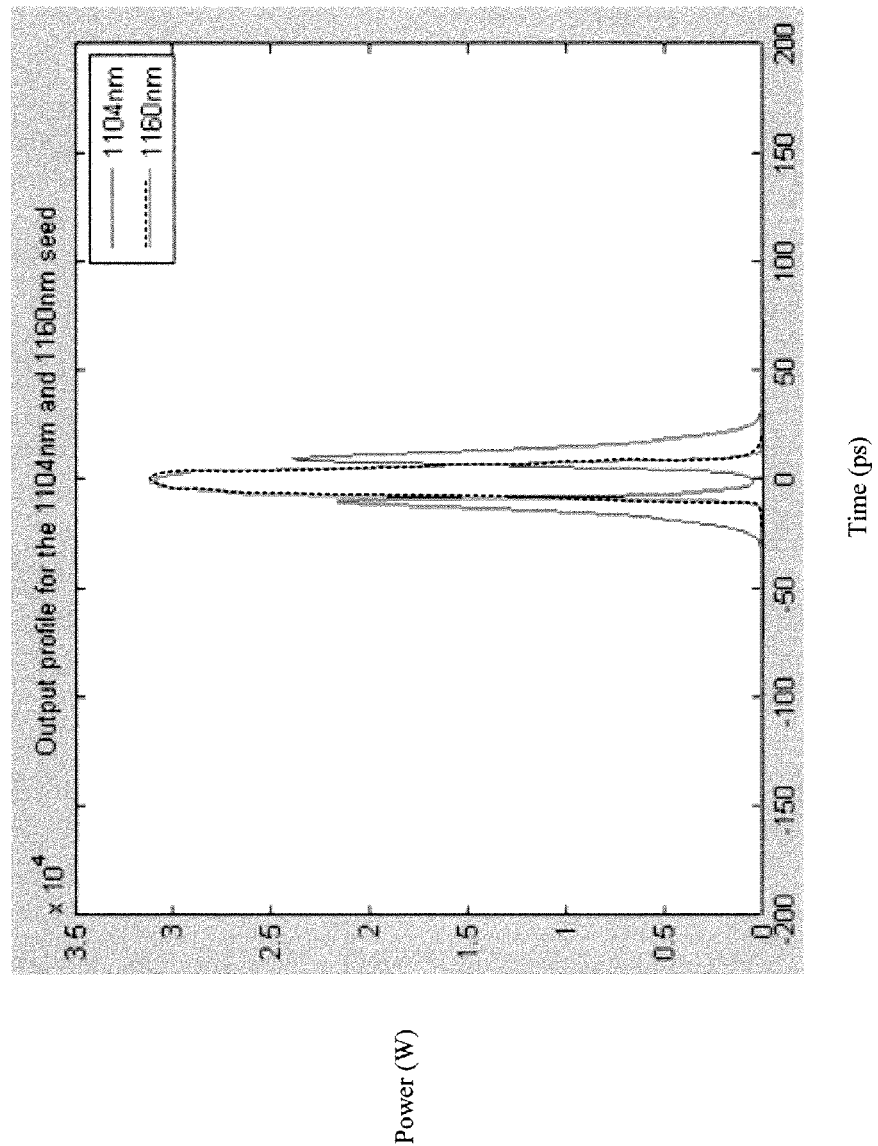

FIG. 3B shows an example of the 1104 nm seed profile at the input to pre-amplification stages 304. In this example, pulsed source 1104 nm has a 20 ps pulse width (full width half maximum FWHM) and 50 W of peak power. FIG. 3C shows the temporal profiles of the 1104 nm light at the output of pre-amplification stages 304. Since there is no 1160 nm Raman signal at this point only the 1104 nm light has been amplified. Using a 100 mW CW seed 302, an exemplary output of power amplifier 305 is shown in FIG. 3D. As can be seen, a significant portion of the 1104 nm light has been changed to 1160 nm light through the Raman process. Additional Raman gain is possible by adding an un-doped portion of Raman gain fiber 306.

Figure 4A:
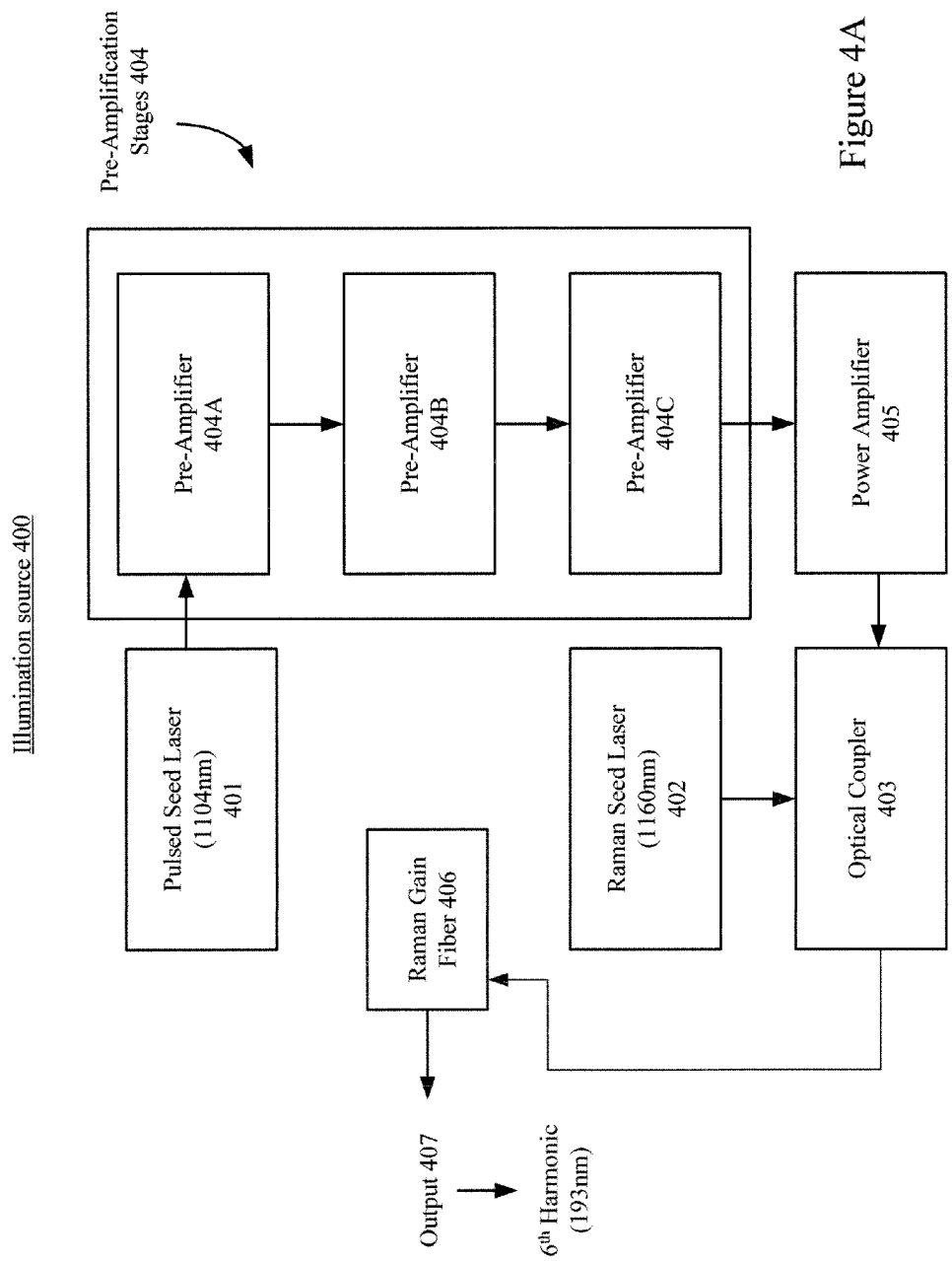
FIG. 4A illustrates a block diagram of yet another fiber-based illumination source, which can generate UV laser light for an inspection system. The illumination source includes a pulsed seed laser having 1104 nm wavelength provided to a plurality of sequentially-connected pre-amplification stages, a power amplifier, and a Raman seed laser having 1160 nm wavelength injected into a Raman gain fiber coupled to an output of the power amplifier.

FIG. 4A illustrates a block diagram of another fiber-based illumination source 400, which can generate UV laser light for an inspection system. Illumination source 400 includes a pulsed seed laser 401 having a wavelength of approximately 1104 nm, which is provided to a plurality of sequentially-coupled pre-amplification stages 404. In the embodiment shown in FIG. 4A, pre-amplification stages 404 include three pre-amplifiers 404A, 404B, and 404C. However, other embodiments of illumination source 400 can include any number of pre-amplifiers depending on the desired output power levels. The output of pre-amplification stages 404 is provided to a power amplifier 405.

In this embodiment, the output of Raman seed laser 402 is combined the output of power amplifier 405 in an optical coupler 403. The output of optical coupler 403 is then provided to a Raman gain fiber 406, which in turn generates an output 407. Thus, this configuration combines a low power Raman seed and high power light from power amplifier 405, thereby eliminating any complications with injecting a separate wavelength before or within the fiber amplifiers of pre-amplification stages 404 or power amplifier 405 (described below in reference to FIGS. 5A, 5B, and 6). Notably, the sixth harmonic of output 407, which is approximately 193 nm, can be generated from output 407.

In one embodiment, the wavelength of 1104 nm is chosen for pulsed seed laser 401 because it will most efficiently pump the Raman gain at 1160 nm. However, because the Raman gain in fused silica is very broad (over 60 nm), it is possible to pump the 1160 nm Raman seed with a wide range of wavelengths. Note that pulsed seed laser 401 can have a variety of pulse widths, repetition rates, peak powers, and pulse shapes. Pulsed seed laser 401 can be a mode-locked laser, a Q-switched laser, a gain-switched laser, or a diode laser. It is also possible to use a continuous wave laser, whose output is then chopped using an electro optic modulator. The use of a continuous wave laser facilitates easy adjustment of the repetition rate, the pulse width, and/or the pulse shape. For example, Raman generation is very efficient with a square pulse shape.

In one preferred embodiment, the Raman seed of Raman seed laser 402 has a wavelength of substantially 1160.2 nm so its $6^{th}$ harmonic will be at substantially 193.4 nm. However it is possible to use different wavelengths and still be within the scope of this invention. In one preferred embodiment, Raman seed laser 402 is a continuous wave laser with a very narrow bandwidth. In other embodiments, Raman seed laser 402 can be a pulsed source synchronized with pulsed seed laser 401.

Figure 4B:
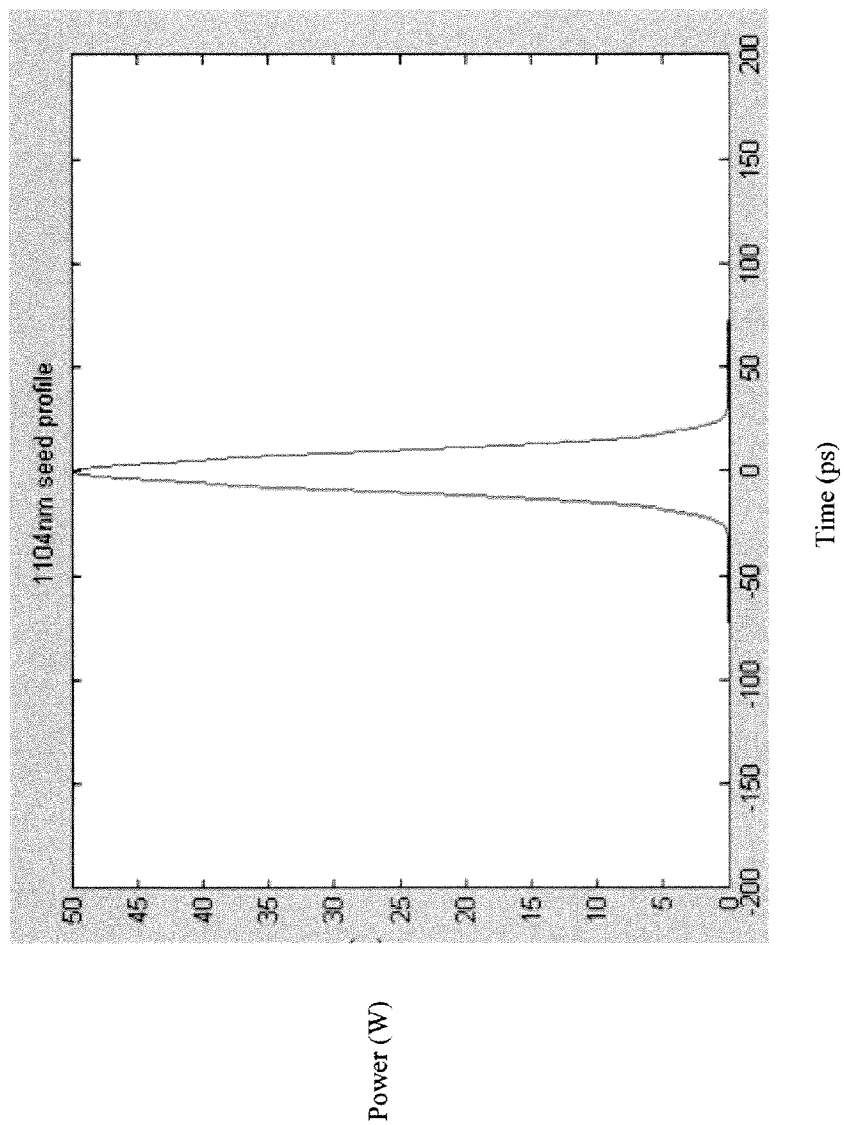
FIGS. 4B, 4C, and 4D illustrate waveforms at three points in the illumination source of FIG. 4A.
Figure 4C:
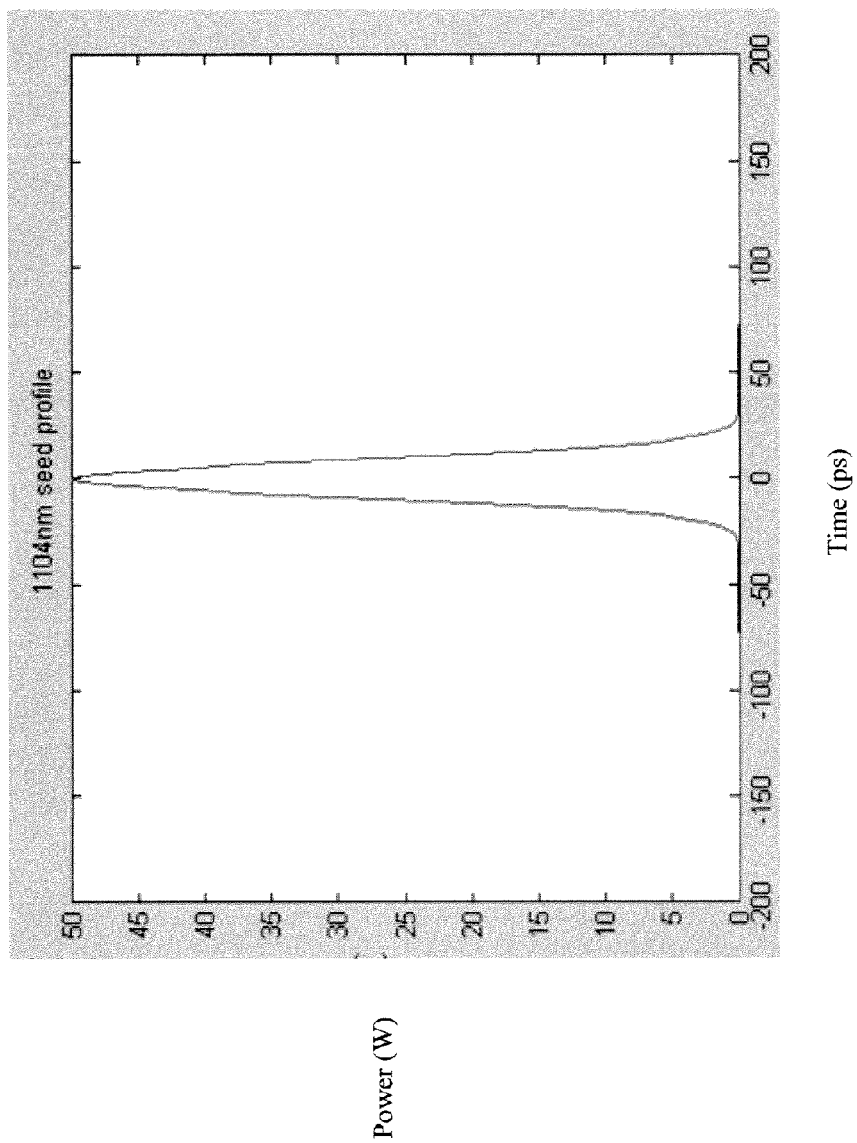
Figure 4D:
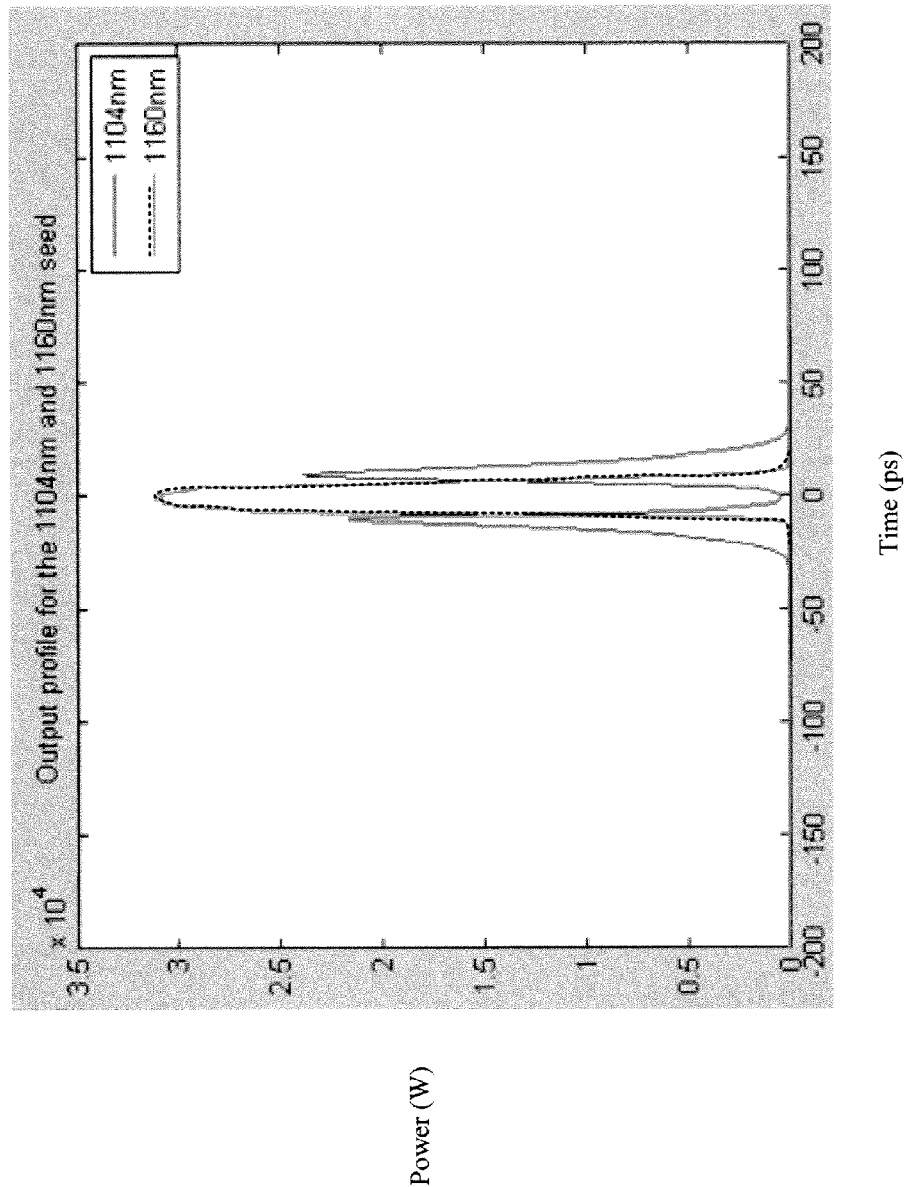

FIG. 4B shows an example of the 1104 nm seed profile at the input to pre-amplification stages 404. In this example, pulsed source 1104 nm has a 20 ps pulse width and 50 W of peak power. FIG. 4C shows the temporal profiles of the 1104 nm light at the output of power amplifier 405. Since there is no 1160 nm Raman signal at this point, only the 1104 nm light has been amplified. Using a 100 mW CW seed 402, the output of Raman gain fiber 406 is shown in FIG. 4D. As can be seen, a significant portion of the 1104 nm light has been changed to 1160 nm light through the Raman process.

FIG. 5A illustrates an exemplary pre-amplifier 500, which can form one of the pre-amplification stages shown in FIGS. 2A, 3A, and 4A. In this embodiment, pre-amplifier 500 includes an amplified spontaneous emission (ASE) filter 501 that receives an input 508 from an upstream component. An optical coupler 502 can combine the output of ASE filter 501 and an output of a pump laser 504 to generate an output. Pump laser 504 is used to transfer energy into the gain medium of fiber amplifier 503. This energy is absorbed by the medium, thereby exciting states in its atoms. Pump laser 504 can be implemented using a laser diode or a fiber laser, which has energy higher than the lasing threshold of input 508. In one embodiment, pump laser 504 can include a plurality of single emitter diodes coupled together. Because a single emitter diode tends to have a relatively long life, such a configuration in pump laser 504 may be advantageous. The pump light of pump laser 504 can be in the range of 800-1000 nm, but can be as long as 1090 nm (this flexibility is possible because a multi-photon process is unnecessary for the pump). The output of optical coupler 502 is provided to a fiber amplifier 503. Fiber amplifier 503 can be core pumped or cladding pumped. Cladding pumping is very common and is a unique property of fiber lasers where pump light propagates in both the core and an un-doped cladding. This allows more uniform pumping along a long length of fiber. Core pumping is done typically when only a very short piece of fiber is used. An output 509 of fiber amplifier 503 can be provided to a downstream component. At high average and high peak powers, the quality of any fused connection can be critical to long term operation. Specifically, any contamination will reduce the lifetime of such a splice. New technologies such as $CO_2$ laser fusing can advantageously enable high power splices with minimal contamination. As described and shown, the configuration of pre-amplifier 500 uses pump light that propagates in the direction of input light propagation.

Note that ASE is light produced by spontaneous emission and is optically amplified by a stimulated emission of a gain medium, such as that of fiber amplifier 503. For example, ASE can be produced when the gain medium of fiber amplifier 503 is pumped by pump laser 502. Excess ASE is undesirable because it limits the maximum gain that can be attained in the gain medium of fiber amplifier 503. ASE filter 501 can advantageously absorb or extract the ASE present in input 508 as well as that generated in pre-amplifier 500. Note that ASE will propagate in both directions in the fiber. These filters have two purposes. The first purpose is to prevent damage to the lower power components due to backward propagating light. The second purpose is to minimize amplification of ASE light in the forward propagation direction. That is, when ASE is amplified, it takes gain away from the 1104 nm light that is desired.

Further note that ASE may also significantly contribute to noise associated with output 509. Therefore, in one preferred embodiment, ASE filter 501 can be configured to effectively reduce broadband spectral ASE background noise to more than 80 dB below the laser line while still transmitting 90% of the single frequency line. This configuration can include a Bragg grating (REG) recorded in a bulk of photosensitive silicate glass or may use other interference filter technology. In some embodiments, further ASE mitigation can be achieved by varying the fiber length or the fiber doping level of fiber amplifier 503. In some embodiments, optical isolators can also be used to limit the impact of ASE.

FIG. 5B illustrates another exemplary pre-amplifier 510, which can form one of the pre-amplification stages shown in FIGS. 2A, 3A, and 4A. In this embodiment, pre-amplifier 510 includes an amplified spontaneous emission (ASE) filter 511 that receives an input 518 from an upstream component. A fiber amplifier 512 can receive the output of ASE filter 511 and generate an output. The output of fiber amplifier 512 can then be combined with an output from a pump laser 513 using an optical coupler 513. Pump laser 514 is used to transfer energy into the gain medium of fiber amplifier 512. This energy is absorbed by the medium, thereby exciting states in its atoms. Pump laser 514 can be implemented using a laser diode or a fiber laser, which has energy higher than the lasing threshold of input 518. In one embodiment, pump laser 514 can include a plurality of single emitter diodes coupled together. Because a single emitter diode tends to have a relatively long life, such a configuration in pump laser 514 may be advantageous. The pump light of pump laser 514 can be in the range of 800-1000 nm, but can be as long as 1090 nm. Fiber amplifier 512 can be core pumped or cladding pumped. An output 519 of optical coupler 513 can be provided to a downstream component. As described and shown, the configuration of pre-amplifier 510 uses pump light that propagates opposite to the direction of input light propagation. This configuration may minimize non-linear effects in various applications. In particular, self-phase modulation (SPM) is a nonlinear effect that caused a broadening of the spectrum in optical fibers. A backward propagating pump can place more of the laser gain toward the output end of the fiber, thereby decreasing the effective nonlinear length.

FIG. 5O illustrates an exemplary pre-amplifier 520, which can be used to implement one of the pre-amplification stages shown in FIGS. 2A, 3A, and 4A. In this embodiment, pre-amplifier 520 includes an ASE filter 521 that can receive an input 528 from an upstream component. A first optical coupler 522 can combine the output of ASE filter 521 and an output of a first pump laser 524. The output of first optical coupler 522 is provided to a fiber amplifier 523. First pump laser 524 can be implemented using a laser diode or a fiber laser, which has energy higher than the lasing threshold of input 528. In one embodiment, pump laser 524 can include a plurality of single emitter diodes coupled together. Because a single emitter diode tends to have a relatively long life, such a configuration in first pump laser 524 may be advantageous.

The pump light of first pump laser 524 can be in the range of 800-1000 nm, but can be as long as 1100 nm. The output of first optical coupler 522 is provided to a fiber amplifier 523. Fiber amplifier 523 can be core pumped or cladding pumped. A second optical coupler 525 can combine an output of fiber amplifier 523 and an output of a second pump laser 526. Second pump laser 526 can be implemented using a laser diode or a fiber laser, which has energy higher than the lasing threshold of the output of fiber amplifier 523. In one embodiment, pump laser 526 can include a plurality of single emitter diodes coupled together. Because a single emitter diode tends to have a relatively long life, such a configuration in second pump laser 526 may be advantageous. The pump light of second pump laser 526 can be in the range of 800-1000 nm, but can be as long as 1100 nm. An output 529 of second optical coupler 525 can be provided to a downstream component. As described and shown, the configuration of pre-amplifier 520 uses pump light that propagates both in the direction of and opposite to the input light propagation, thereby allowing more uniform pumping of long fibers. This can be an issue with long wavelengths, e.g. around 1104 nm, because the gain of Yb is quite low. In such cases, typical pre-amplifiers may be quite long, e.g. on the order of tens of meters long, but can be effectively pumped in two directions to reduce this length.

Figure 5C:
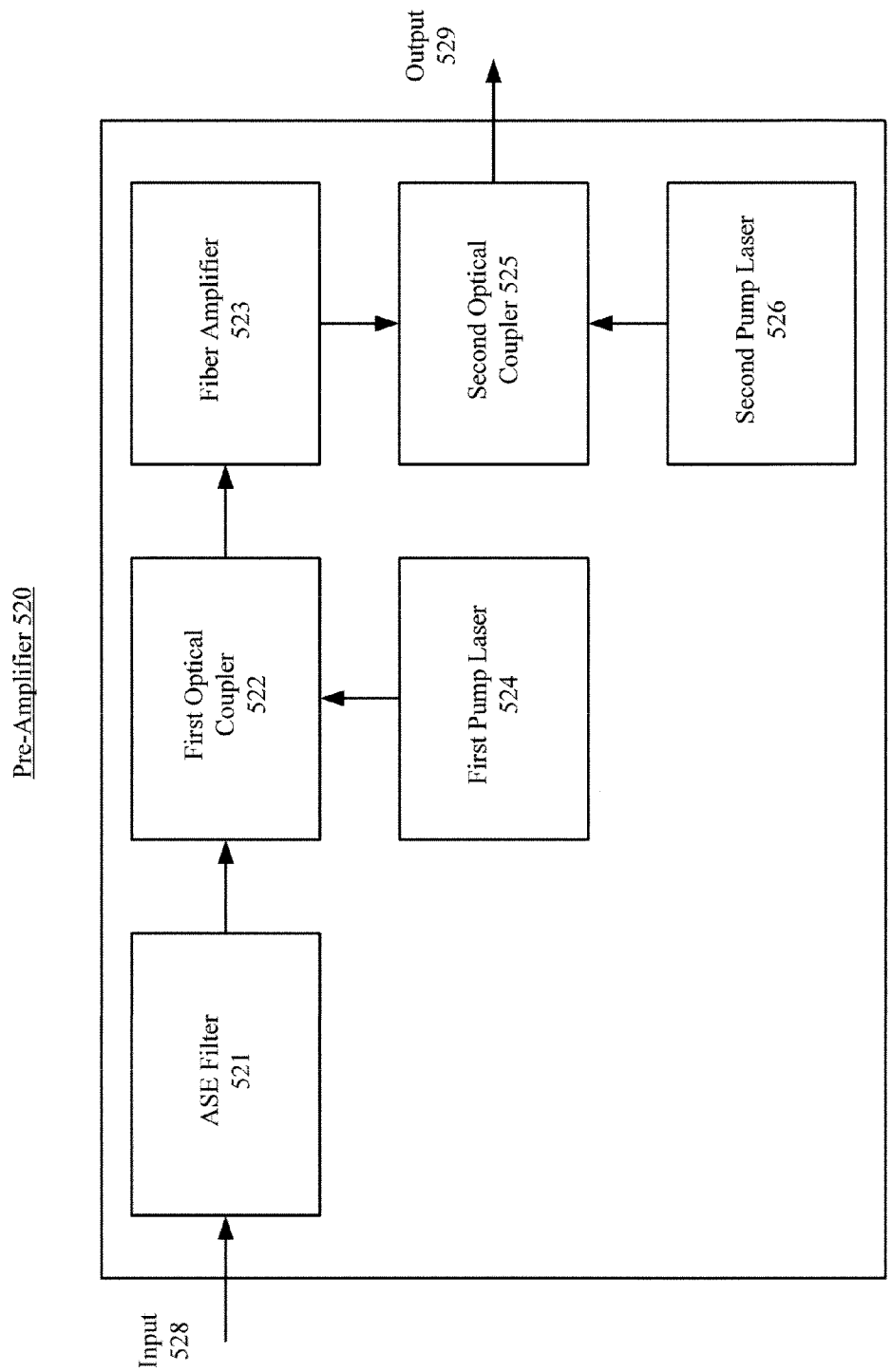
FIG. 5C illustrates a block diagram of another exemplary pre-amplifier that can be used in the fiber-based illumination sources of FIGS. 2A, 3A, and 4A.

Note that any of pre-amplifiers 500, 510, and 520 (shown in FIGS. 5A, 5B, and 5C, respectively) can be used to implement any one of the illumination sources 200, 300, and 400 (shown in FIGS. 2, 3, and 4, respectively). For example, in one embodiment, pre-amplifiers 404A, 404B, and 404C (FIG. 4A) could be implemented using the configuration of pre-amplifier 500 (FIG. 5A) only. In another embodiment, pre-amplifiers 404A, 404B, and 404C could be implemented using the configurations of pre-amplifiers 500, 510, and 520, respectively (FIGS. 5A, 5B, and 5C, respectively). In yet another embodiment, pre-amplifier 404A could be implemented using the configurations of pre-amplifier 500, and pre-amplifiers 404B and 404C could be implemented using the configuration of pre-amplifier 520. Thus, it is readily appreciated that any combination of the exemplary pre-amplifiers can be used in the above-described improved illumination sources.

FIG. 6 shows an exemplary geometry of a power amplifier 600. In this embodiment, the architecture of power amplifier 600 is similar to that of pre-amplifier 520. However, power amplifiers, like pre-amplifiers, can be pumped in the forward direction, the backward direction, or both directions (shown). Thus, in other embodiments, the architecture of exemplary power amplifiers could be the same as that shown for pre-amplifiers 500 or 510. Note that a power amplifier is designed for extracting power, whereas a pre-amplifier is designed to focus mostly on high gain. Therefore, typically, the fiber diameters in a power amplifier are larger than those of the pre-amplifiers to provide as much volume as possible to extract energy.

Figure 7:
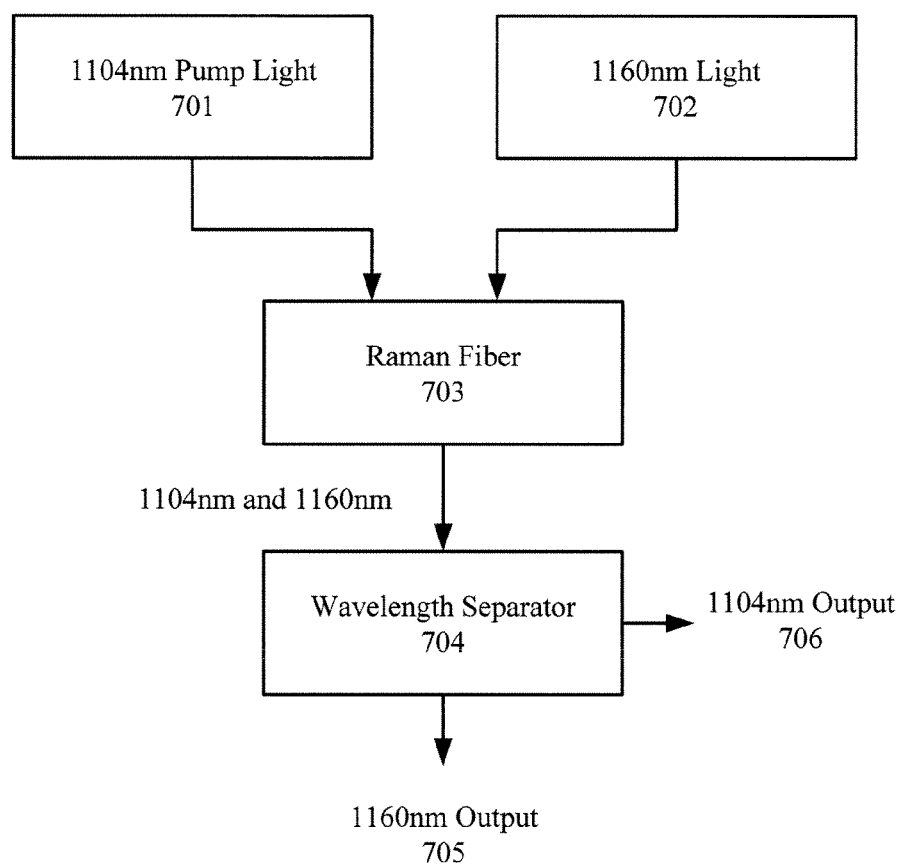
FIG. 7 illustrates a block diagram of an exemplary configuration of a Raman gain fiber.

FIG. 7 illustrates an exemplary Raman gain fiber 700, which includes any type of Raman fiber 703 that can provide the desired Raman gain. In one embodiment, a fiber that does not amplify the 1104 nm pump light 701 can be used. Raman fiber 703 can be fused silica or other glass material. It can also be doped with materials like Germanium to improve the Raman gain. It is also possible to use fibers with photonic crystal structures. In addition to fibers, it is possible to use crystal materials (not shown for simplicity) to generate other Raman wavelengths. Input pump light 701 at 1104 nm along with a Raman seed or amplified signal 702 at 1160 nm is input to Raman fiber 703. Energy from the 1104 nm pump light is transferred to the Raman signal at 1160 nm. After Raman fiber 703, the two wavelengths may be separated using a wavelength separator 704. This wavelength separator 704 can be a dichroic coating, a diffraction grating, etalon, volume Bragg grating, or other similar wavelength selective technique.

FIGS. 8-15 illustrate systems that can include one of the above-described illumination sources. These systems can be used in photomask, reticle, or wafer inspection applications.

Figure 8:
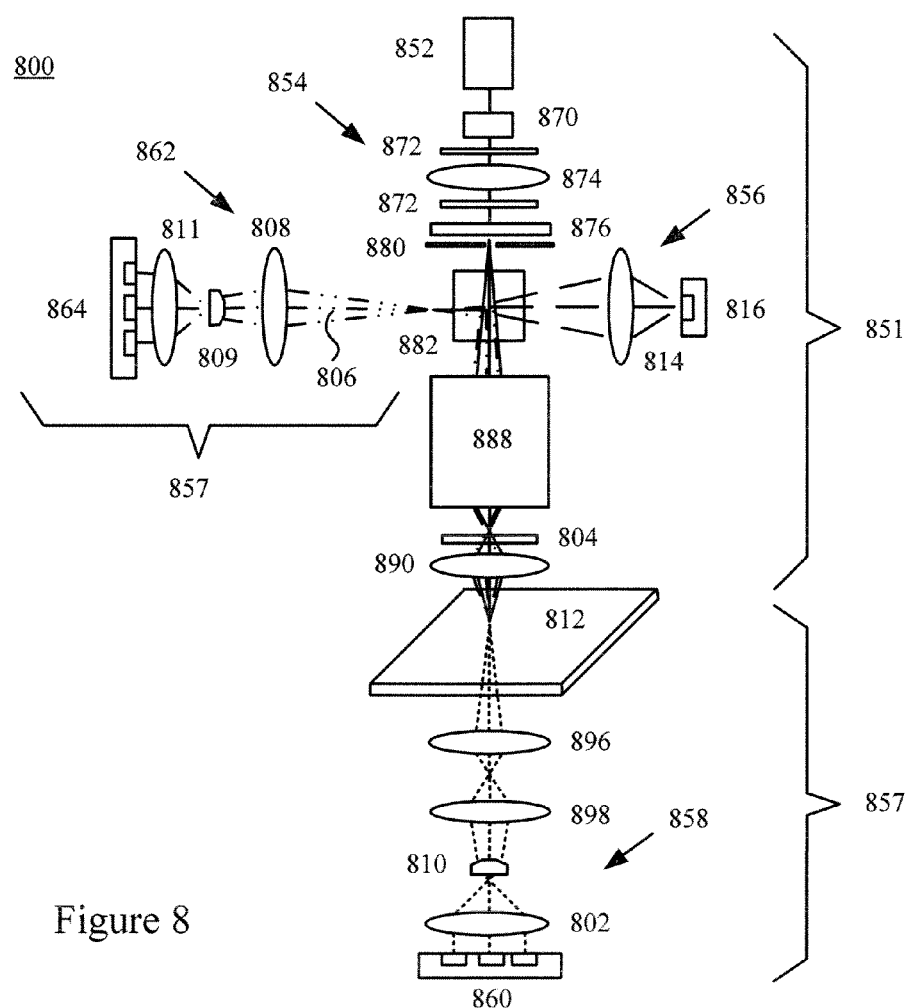
FIG. 8 illustrates an exemplary optical inspection system including one of the above-described improved illumination sources for inspecting the surface of a substrate.

FIG. 8 illustrates an exemplary optical inspection system 800 for inspecting the surface of a substrate 812. System 800 generally includes a first optical arrangement 851 and a second optical arrangement 857. As shown, first optical arrangement 851 includes at least a light source 852, inspection optics 854, and reference optics 856, while the second optical arrangement 857 includes at least transmitted light optics 858, transmitted light detectors 860, reflected light optics 862, and reflected light detectors 864. In one preferred configuration, light source 852 includes one of the above-described illumination sources.

Light source 852 is configured to emit a light beam that passes through an acousto-optic device 870, which is arranged for deflecting and focusing the light beam. Acousto-optic device 870 may include a pair of acousto-optic elements, e.g. an acousto-optic pre-scanner and an acousto-optic scanner, which deflect the light beam in the Y-direction and focus it in the Z-direction. By way of example, most acousto-optic devices operate by sending an RF signal to quartz or a crystal such as $TeO_2$. This RF signal causes a sound wave to travel through the crystal. Because of the travelling sound wave, the crystal becomes asymmetric, which causes the index of refraction to change throughout the crystal. This change causes incident beams to form a focused travelling spot which is deflected in an oscillatory fashion.

When the light beam emerges from acousto-optic device 870, it then passes through a pair of quarter wave plates 872 and a relay lens 874. Relay lens 874 is arranged to collimate the light beam. The collimated light beam then continues on its path until it reaches a diffraction grating 876. Diffraction grating 876 is arranged for flaring out the light beam, and more particularly for separating the light beam into three distinct beams, which are spatially distinguishable from one another (i.e. spatially distinct). In most cases, the spatially distinct beams are also arranged to be equally spaced apart and have substantially equal light intensities.

Upon leaving the diffraction grating 876, the three beams pass through an aperture 880 and then continue until they reach a beam splitter cube 882. Beam splitter cube 882 (in combination with the quarter wave plates 872) is arranged to divide the beams into two paths, i.e. one directed downward and the other directed to the right (in the configuration shown in FIG. 8). The path directed downward is used to distribute a first light portion of the beams to substrate 812, whereas the path directed to the right is used to distribute a second light portion of the beams to reference optics 856. In most embodiments, most of the light is distributed to substrate 812 and a small percentage of the light is distributed to reference optics 856, although the percentage ratios may vary according to the specific design of each optical inspection system. In one embodiment, reference optics 856 can include a reference collection lens 814 and a reference detector 816. Reference collection lens 814 is arranged to collect and direct the portion of the beams on reference detector 816, which is arranged to measure the intensity of the light. Reference optics are generally well known in the art and for the sake of brevity will not be discussed in detail.

The three beams directed downward from beam splitter 882 are received by a telescope 888, which includes several lens elements that redirect and expand the light. In one embodiment, telescope 888 is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From telescope 888, the three beams pass through an objective lens 890, which is arranged for focusing the beams onto the surface of substrate 812. As the beams intersect the surface as three distinct spots, both reflected light beams and transmitted light beams may be generated. The transmitted light beams pass through substrate 812, while the reflected light beams reflect off the surface. By way of example, the reflected light beams may reflect off of opaque surfaces of the substrate, and the transmitted light beams may transmit through transparent areas of the substrate. The transmitted light beams are collected by transmitted light optics 858 and the reflected beams are collected by reflected light optics 862.

With regards to transmitted light optics 858, the transmitted light beams, after passing through substrate 812, are collected by a first transmitted lens 896 and focused with the aid of a spherical aberration corrector lens 898 onto a transmitted prism 810. Prism 810 can be configured to have a facet for each of the transmitted light beams that are arranged for repositioning and bending the transmitted light beams. In most cases, prism 810 is used to separate the beams so that they each fall on a single detector in transmitted light detector arrangement 860 (shown as having three distinct detectors). Accordingly, when the beams leave prism 810, they pass through a second transmitted lens 802, which individually focuses each of the separated beams onto one of the three detectors, each of which is arranged for measuring the intensity of the transmitted light.

With regards to reflected light optics 862, the reflected light beams after reflecting off of substrate 812 are collected by objective lens 890, which then directs the beams towards telescope 888. Before reaching telescope 888, the beams also pass through a quarter wave plate 804. In general terms, objective lens 890 and telescope 888 manipulate the collected beams in a manner that is optically reverse in relation to how the incident beams are manipulated. That is, objective lens 890 re-collimates the beams, and telescope 888 reduces their size. When the beams leave telescope 888, they continue (backwards) until they reach beam splitter cube 882. Beam splitter 882 is configured to work with quarter wave-plate 804 to direct the beams onto a central path 806.

The beams continuing on path 806 are then collected by a first reflected lens 808, which focuses each of the beams onto a reflected prism 809, which includes a facet for each of the reflected light beams. Reflected prism 809 is arranged for repositioning and bending the reflected light beams. Similar to transmitted prism 810, reflected prism 809 is used to separate the beams so that they each fall on a single detector in the reflected light detector arrangement 864. As shown, reflected light detector arrangement 864 includes three individually distinct detectors. When the beams leave reflected prism 809, they pass through a second reflected lens 811, which individually focuses each of the separated beams onto one of these detectors, each of which is arranged for measuring the intensity of the reflected light.

There are multiple inspection modes that can be facilitated by the aforementioned optical assembly. By way of example, the optical assembly can facilitate a transmitted light inspection mode, a reflected light inspection mode, and a simultaneous inspection mode. With regards to the transmitted light inspection mode, transmission mode detection is typically used for defect detection on substrates such as conventional optical masks having transparent areas and opaque areas. As the light beams scan the mask (or substrate 812), the light penetrates the mask at transparent points and is detected by the transmitted light detectors 860, which are located behind the mask and which measure the intensity of each of the light beams collected by transmitted light optics 858 including first transmitted lens 896, second transmitted lens 802, spherical aberration lens 898, and prism 810.

With regards to the reflected light inspection mode, reflected light inspection can be performed on transparent or opaque substrates that contain image information in the form of chromium, developed photoresist or other features. Light reflected by the substrate 812 passes backwards along the same optical path as inspection optics 854, but is then diverted by a polarizing beam splitter 882 into detectors 864. More particularly, first reflected lens 808, prism 809, and second reflected lens 811 project the light from the diverted light beams onto detectors 864. Reflected light inspection may also be used to detect contamination on top of opaque substrate surfaces.

With regards to the simultaneous inspection mode, both transmitted light and reflected light are utilized to determine the existence and/or type of a defect. The two measured values of the system are the intensity of the light beams transmitted through substrate 812 as sensed by transmitted light detectors 860 and the intensity of the reflected light beams as detected by reflected light detectors 864. Those two measured values can then be processed to determine the type of defect, if any, at a corresponding point on substrate 812.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect were examined. In addition, one may determine signatures for certain types of defects, such as the ratio of their reflected and transmitted light intensities. This information can then be used to automatically classify defects. U.S. Pat. No. 5,563, 702, which issued on Oct. 8, 1996 and is incorporated by reference herein, describes additional details regarding system 800.

In accordance with certain embodiments of the present invention an inspection system that incorporates an approximately 193 nm laser system may simultaneously detect two channels of data on a single detector. Such an inspection system may be used to inspect a substrate such as a reticle, a photomask or a wafer, and may operate as described in U.S. Pat. No. 7,528,943, which issued on May 5, 2009 to Brown et al, and is incorporated by reference herein.

Figure 9:
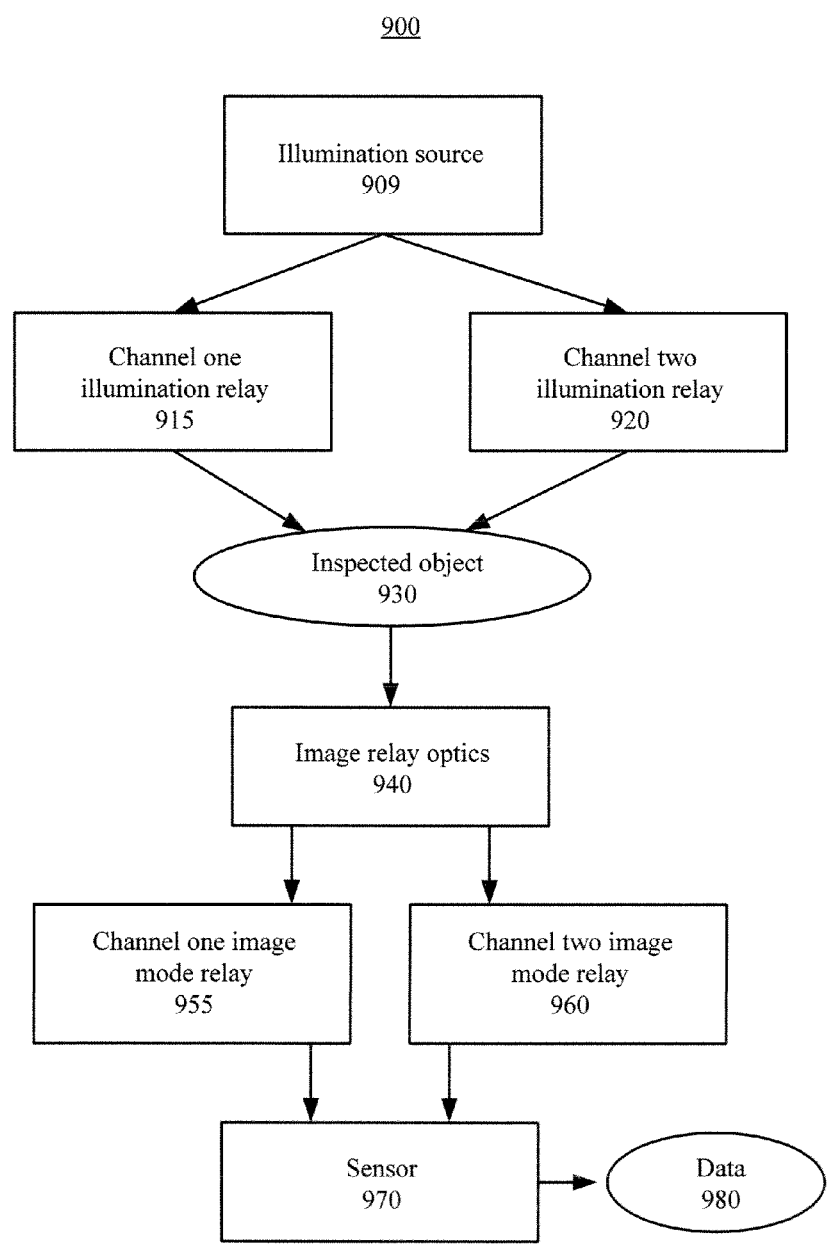
FIG. 9 shows a reticle, photomask or wafer inspection system including one of the above-described improved illumination sources that simultaneously detects two channels of image or signal on one sensor.

FIG. 9 shows a reticle, photomask or wafer inspection system 900 that simultaneously detects two channels of image or signal on one sensor 970. The illumination source 909 incorporates a 193.4 nm laser system as described herein. The light source may further comprise a pulse multiplier and/or a coherence reducing scheme. The two channels may comprise reflected and transmitted intensity when an inspected object 930 is transparent (for example a reticle or photomask), or may comprise two different illumination modes, such as angles of incidence, polarization states, wavelength ranges or some combination thereof.

As shown in FIG. 9, illumination relay optics 915 and 920 relay the illumination from source 909 to the inspected object 930. The inspected object 930 may be a reticle, a photomask, a semiconductor wafer or other article to be inspected. Image relay optics 955 and 960 relay the light that is reflected and/or transmitted by the inspected object 930 to the sensor 970. The data corresponding to the detected signals or images for the two channels is shown as data 980 and is transmitted to a computer (not shown) for processing.

Figure 10:
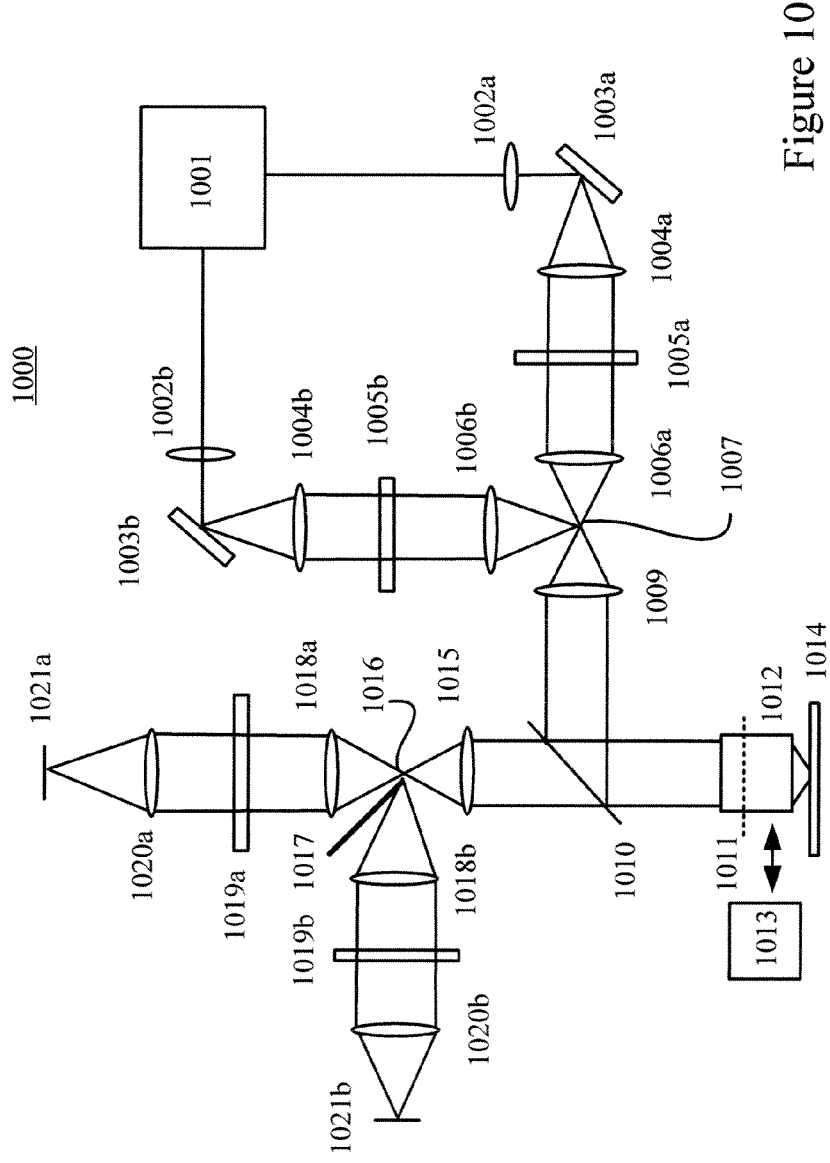
FIG. 10 illustrates an exemplary inspection system including multiple objectives and one of the above-described improved illumination sources.

FIG. 10 illustrates an exemplary inspection system 1000 including multiple objectives and one of the above-described illumination sources. In system 1000, illumination from a laser source 1001 is sent to multiple sections of the illumination subsystem. A first section of the illumination subsystem includes elements 1002a through 1006a. Lens 1002a focuses light from laser 1001. Light from lens 1002a then reflects from mirror 1003a. Mirror 1003a is placed at this location for the purposes of illustration, and may be positioned elsewhere. Light from mirror 1003a is then collected by lens 1004a, which forms illumination pupil plane 1005a. An aperture, filter, or other device to modify the light may be placed in pupil plane 1005a depending on the requirements of the inspection mode. Light from pupil plane 1005a then passes through lens 1006a and forms illumination field plane 1007.

A second section of the illumination subsystem includes elements 1002b through 1006b. Lens 1002b focuses light from laser 1001. Light from lens 1002b then reflects from mirror 1003b. Light from mirror 1003b is then collected by lens 1004b which forms illumination pupil plane 1005b. An aperture, filter, or other device to modify the light may be placed in pupil plane 1005b depending on the requirements of the inspection mode. Light from pupil plane 1005b then passes through lens 1006b and forms illumination field plane 1007. The light from the second section is then redirected by mirror or reflective surface such that the illumination field light energy at illumination field plane 1007 is comprised of the combined illumination sections.

Field plane light is then collected by lens 1009 before reflecting off a beamsplitter 1010. Lenses 1006a and 1009 form an image of first illumination pupil plane 1005a at objective pupil plane 1011. Likewise, lenses 1006b and 1009 form an image of second illumination pupil plane 1005b at objective pupil plane 1011. An objective 1012 (or alternatively 1013) then takes the pupil light and forms an image of illumination field 1007 at sample 1014. Objective 1012 or objective 1013 can be positioned in proximity to sample 1014. Sample 1014 can move on a stage (not shown), which positions the sample in the desired location. Light reflected and scattered from the sample 1014 is collected by the high NA catadioptric objective 1012 or objective 1013. After forming a reflected light pupil at objective pupil plane 1011, light energy passes beamsplitter 1010 and lens 1015 before forming an internal field 1016 in the imaging subsystem. This internal imaging field is an image of sample 1014 and correspondingly illumination field 1007. This field may be spatially separated into multiple fields corresponding to the illumination fields. Each of these fields can support a separate imaging mode.

One of these fields can be redirected using mirror 1017. The redirected light then passes through lens 1018b before forming another imaging pupil 1019b. This imaging pupil is an image of pupil 1011 and correspondingly illumination pupil 1005b. An aperture, filter, or other device to modify the light may be placed in pupil plane 1019b depending on the requirements of the inspection mode. Light from pupil plane 1019b then passes through lens 1020b and forms an image on sensor 1021b. In a similar manner, light passing by mirror or reflective surface 1017 is collected by lens 1018a and forms imaging pupil 1019a. Light from imaging pupil 1019a is then collected by lens 1020a before forming an image on detector 1021a. Light imaged on detector 1021a can be used for a different imaging mode from the light imaged on sensor 1021b.

The illumination subsystem employed in system 1000 is composed of laser source 1001, collection optics 1002-1004, beam shaping components placed in proximity to a pupil plane 1005, and relay optics 1006 and 1009. An internal field plane 1007 is located between lenses 1006 and 1009. In one preferred configuration, laser source 1001 can include one of the above-described illumination sources.

With respect to laser source 1001, while illustrated as a single uniform block having two points or angles of transmission, in reality this represents a laser source able to provide two channels of illumination, for example a first channel of light energy such as laser light energy at a first frequency which passes through elements 1002a-1006a, and a second channel of light energy such as laser light energy at a second frequency which passes through elements 1002b-1006b. Different light energy modes may be employed, such as bright field energy in one channel and a dark field mode in the other channel.

While light energy from laser source 1001 is shown to be emitted 90 degrees apart, and the elements 1002a-1006a and 1002b-1006b are oriented at 90 degree angles, in reality light may be emitted at various orientations, not necessarily in two dimensions, and the components may be oriented differently than as shown. FIG. 10 is therefore simply a representation of the components employed and the angles or distances shown are not to scale nor specifically required for the design.

Elements placed in proximity to pupil plane 1005 may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 1005a, 1005b, 1019a, and 1019b.

Multiple objectives may also be used as shown in FIG. 10. For example, although two objectives 1012 and 1013 are shown, any number is possible. Each objective in such a design may be optimized for each wavelength produced by laser source 1001. These objectives 1012 and 1013 can either have fixed positions or be moved into position in proximity to the sample 1014. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be higher. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 1015. The purpose of the image forming optics 1015 is to form an internal image 1016 of sample 1014. At this internal image 1016, a mirror 1017 can be placed to redirect light corresponding to one of the inspection modes. It is possible to redirect the light at this location because the light for the imaging modes are spatially separate. The image forming optics 1018 (1018a and 1018b) and 1020 (1020a and 1020b) can be implemented in several different forms including a varifocal zoom, multiple afocal tube lenses with focusing optics, or multiple image forming mag tubes. U.S. Published Application 2009/0180176, which published on Jul. 16, 2009 and is incorporated by reference herein, describes additional details regarding system 1000.

Figure 11:
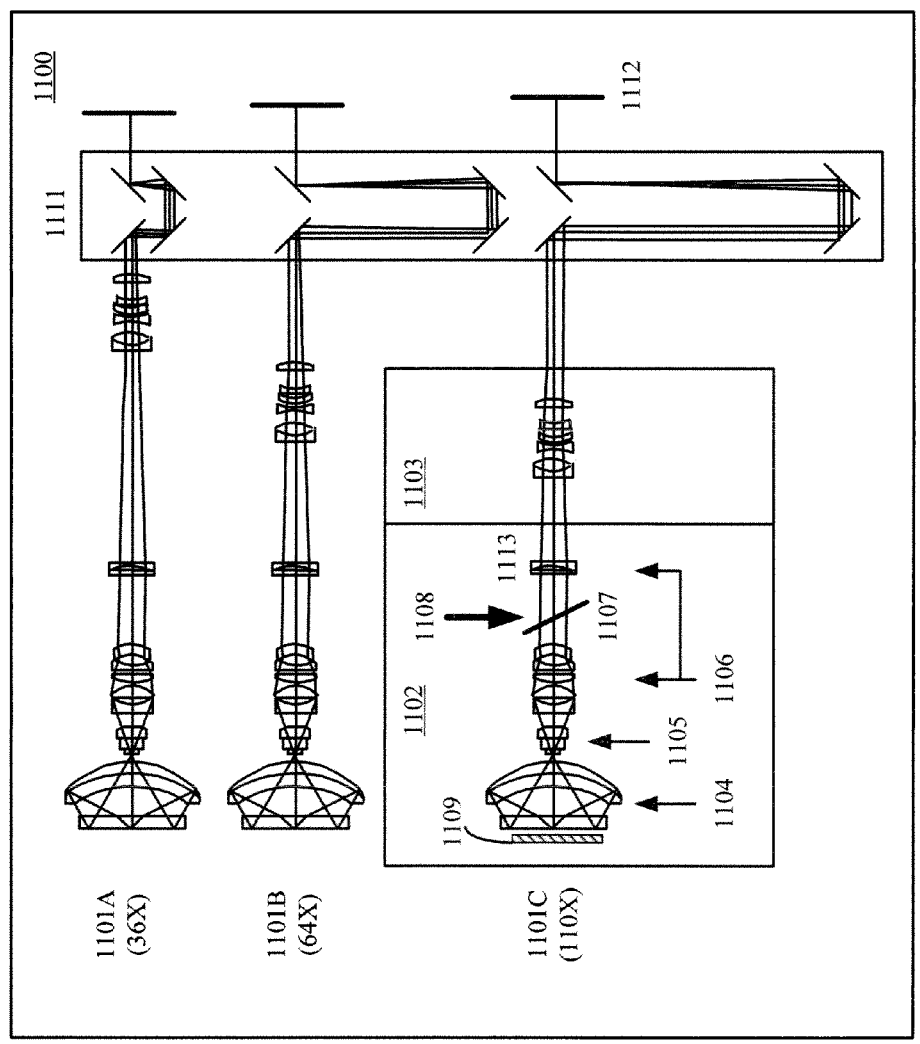
FIG. 11 illustrates an exemplary ultra-broadband UV microscope imaging system including three sub-sections, each including one of the above-described improved illumination sources.

FIG. 11 illustrates an exemplary ultra-broadband UV microscope imaging system 1100 including three sub-sections 1101A, 1101B, and 1101C. Sub-section 1101C includes a catadioptric objective section 1102 and a zooming tube lens 1103. Catadioptric objective section 1102 includes a catadioptric lens group 1104, a field lens group 1105, and a focusing lens group 1106. System 1100 can image an object/sample 1109 (e.g. a wafer being inspected) to an image plane 1112.

Catadioptric lens group 1104 includes a near planar (or planar) reflector (which is a reflectively coated lens element), a meniscus lens (which is a refractive surface), and a concave spherical reflector. Both reflective elements can have central optical apertures without reflective material to allow light from an intermediate image plane to pass through the concave spherical reflector, be reflected by the near planar (or planar) reflector onto the concave spherical reflector, and pass back through the near planar (or planar) reflector, traversing the associated lens element or elements on the way. Catadioptric lens group 1104 is positioned to form a real image of the intermediate image, such that, in combination with zooming tube lens 1103, primary longitudinal color of the system is substantially corrected over the wavelength band.

Field lens group 1105 can be made from two or more different refractive materials, such as fused silica and fluoride glass, or diffractive surfaces. Field lens group 1105 may be optically coupled together or alternatively may be spaced slightly apart in air. Because fused silica and fluoride glass do not differ substantially in dispersion in the deep ultraviolet range, the individual powers of the several component element of the field lens group need to be of high magnitude to provide different dispersions. Field lens group 1105 has a net positive power aligned along the optical path proximate to the intermediate image. Use of such an achromatic field lens allows the complete correction of chromatic aberrations including at least secondary longitudinal color as well as primary and secondary lateral color over an ultra-broad spectral range. In one embodiment, only one field lens component need be of a refractive material different than the other lenses of the system.

Focusing lens group 1106 includes multiple lens elements, preferably all formed from a single type of material, with refractive surfaces having curvatures and positions selected to correct both monochromatic aberrations and chromatic variation of aberrations and focus light to an intermediate image. In one embodiment of focusing lens group 1106, a combination of lenses 1113 with low power corrects for chromatic variation in spherical aberration, coma, and astigmatism. A beam splitter 1107 provides an entrance for a UV light source 1108. UV light source 1108 can advantageously be implemented by the above-described illumination source described above.

Zooming tube lens 1103 can be all the same refractive material, such as fused silica, and is designed so that primary longitudinal and primary lateral colors do not change during zooming. These primary chromatic aberrations do not have to be corrected to zero, and cannot be if only one glass type is used, but they have to be stationary, which is possible. Then the design of the catadioptric objective section 1102 must be modified to compensate for these uncorrected but stationary chromatic aberrations of zooming tube lens 1103. Zooming tube lens 1103, which can zoom or change magnification without changing its higher-order chromatic aberrations, includes lens surfaces disposed along an optical path of the system.

In one preferred embodiment, zooming tube lens 1003 is first corrected independently of catadioptric objective 1102 section using two refractive materials (such as fused silica and calcium fluoride). Zooming tube lens 1103 is then combined with catadioptric objective section 1102, at which time catadioptric objective section 1102 can be modified to compensate for the residual higher-order chromatic aberrations of system 1100. This compensating is possible because of field lens group 1105 and low power lens group 1113. The combined system is then optimized with all parameters being varied to achieve the best performance.

Note that sub-sections 1101A and 1101B include substantially similar components to that of sub-section 1201C and therefore are not discussed in detail.

System 1100 includes a folding mirror group 1111 to provide linear zoom motion that allows a zoom from 36× to 100×. The wide range zoom provides continuous magnification change, whereas the fine zoom reduces aliasing and allows electronic image processing, such as cell-to-cell subtraction for a repeating image array. Folding mirror group 1111 can be characterized as a "trombone" system of reflective elements. Zooming is done by moving the group of zooming tube lens 1103, as a unit, and also moving the arm of the trombone slide. Because the trombone motion only affects focus and the f# speed at its location is very slow, the accuracy of this motion could be very loose. One advantage of this trombone configuration is that it significantly shortens the system. Another advantage is that there is only one zoom motion that involves active (non-flat) optical elements. And the other zoom motion, with the trombone slide, is insensitive to errors. U.S. Pat. No. 5,999,310, which issued on Dec. 7, 1999 and is incorporated by reference herein, describes system 1100 in further detail.

Figure 12:
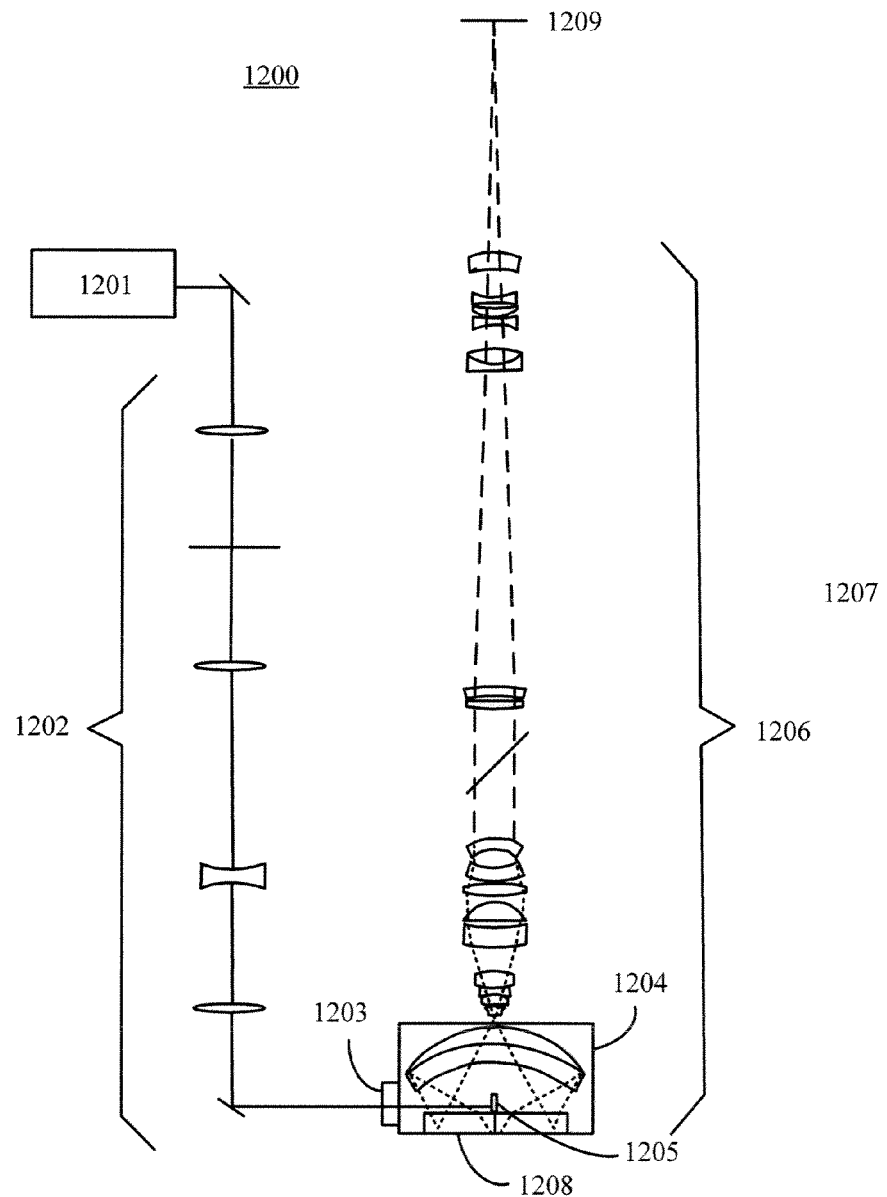
FIG. 12 illustrates the addition of a normal incidence laser illumination (dark-field or bright-field) to a catadioptric imaging system including one of the above-described improved illumination sources.

FIG. 12 illustrates the addition of a normal incidence laser illumination (dark-field or bright-field) to a catadioptric imaging system 1200. The illumination block of system 1200 includes a laser 1201, adaptation optics 1202 to control the illumination beam size and profile on the surface being inspected, an aperture and window 1203 in a mechanical housing 1204, and a prism 1205 to redirect the laser along the optical axis at normal incidence to the surface of a sample 1208. Prism 1205 also directs the specular reflection from surface features of sample 1208 and reflections from the optical surfaces of an objective 1206 along the optical path to an image plane 1209. Lenses for objective 1206 can be provided in the general form of a catadioptric objective, a focusing lens group, and a zooming tube lens section (see, e.g. FIG. 11). In a preferred embodiment, laser 1201 can be implemented by the above-described above-described illumination source. Published Patent Application 2007/0002465, which published on Jan. 4, 2007 and is incorporated by reference herein, describes system 1200 in further detail.

Figure 13A:
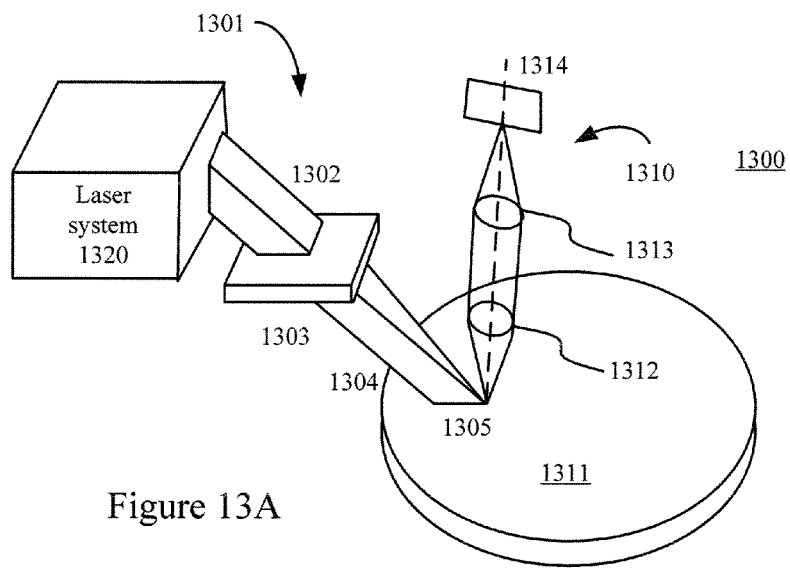
FIG. 13A illustrates a surface inspection apparatus that includes an illumination system including one of the above-described improved illumination sources and a collection system for inspecting areas of a surface.

FIG. 13A illustrates a surface inspection apparatus 1300 that includes illumination system 1301 and collection system 1310 for inspecting areas of surface 1311. As shown in FIG. 13A, a laser system 1320 directs a light beam 1302 through a lens 1303. In a preferred embodiment, laser system 1320 includes the above-described illumination source, an annealed crystal, and a housing to maintain the annealed condition of the crystal during standard operation at a low temperature. First beam shaping optics can be configured to receive a beam from the laser and focus the beam to an elliptical cross section at a beam waist in or proximate to the crystal.

Lens 1303 is oriented so that its principal plane is substantially parallel to a sample surface 1311 and, as a result, illumination line 1305 is formed on surface 1311 in the focal plane of lens 1303. In addition, light beam 1302 and focused beam 1304 are directed at a non-orthogonal angle of incidence to surface 1311. In particular, light beam 1302 and focused beam 1304 may be directed at an angle between about 1 degree and about 85 degrees from a normal direction to surface 1311. In this manner, illumination line 1305 is substantially in the plane of incidence of focused beam 1304.

Collection system 1310 includes lens 1312 for collecting light scattered from illumination line 1305 and lens 1313 for focusing the light coming out of lens 1312 onto a device, such as charge coupled device (CCD) 1314, comprising an array of light sensitive detectors. In one embodiment, CCD 1314 may include a linear array of detectors. In such cases, the linear array of detectors within CCD 1314 can be oriented parallel to illumination line 1315. In one embodiment, multiple collection systems can be included, wherein each of the collection systems includes similar components, but differ in orientation.

Figure 13B:
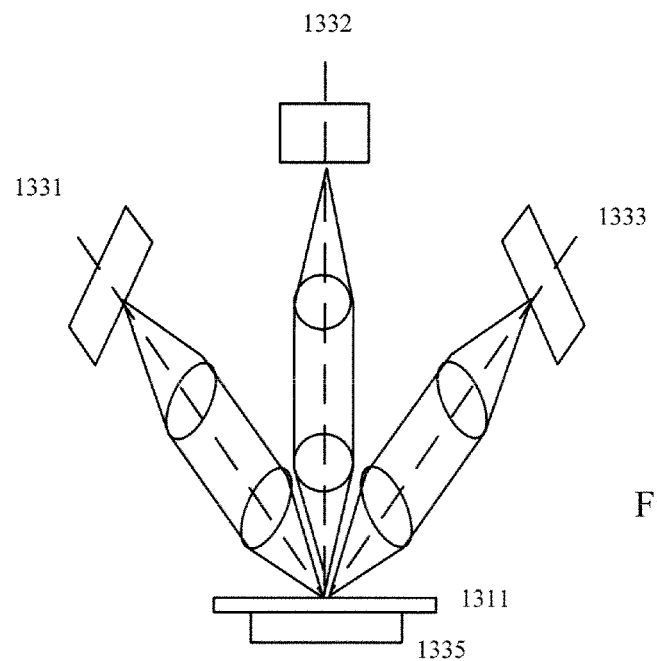
FIG. 13B illustrates an exemplary array of multiple collection systems for a surface inspection apparatus including one of the above-described improved illumination sources.

For example, FIG. 13B illustrates an exemplary array of collection systems 1331, 1332, and 1333 for a surface inspection apparatus (wherein its illumination system, e.g. similar to that of illumination system 1301, is not shown for simplicity). First optics in collection system 1331 collect light scattered in a first direction from the surface of sample 1311. Second optics in collection system 1332 collect light scattered in a second direction from the surface of sample 1311. Third optics in collection system 1333 collect light scattered in a third direction from the surface of sample 1311. Note that the first, second, and third paths are at different angles of reflection to said surface of sample 1311. A platform 1335 supporting sample 1311 can be used to cause relative motion between the optics and sample 1311 so that the whole surface of sample 1311 can be scanned. U.S. Pat. No. 7,525,649, which issued on Apr. 28, 2009 and is incorporated by reference herein, describes surface inspection apparatus 1300 and other multiple collection systems in further detail.

Figure 14:
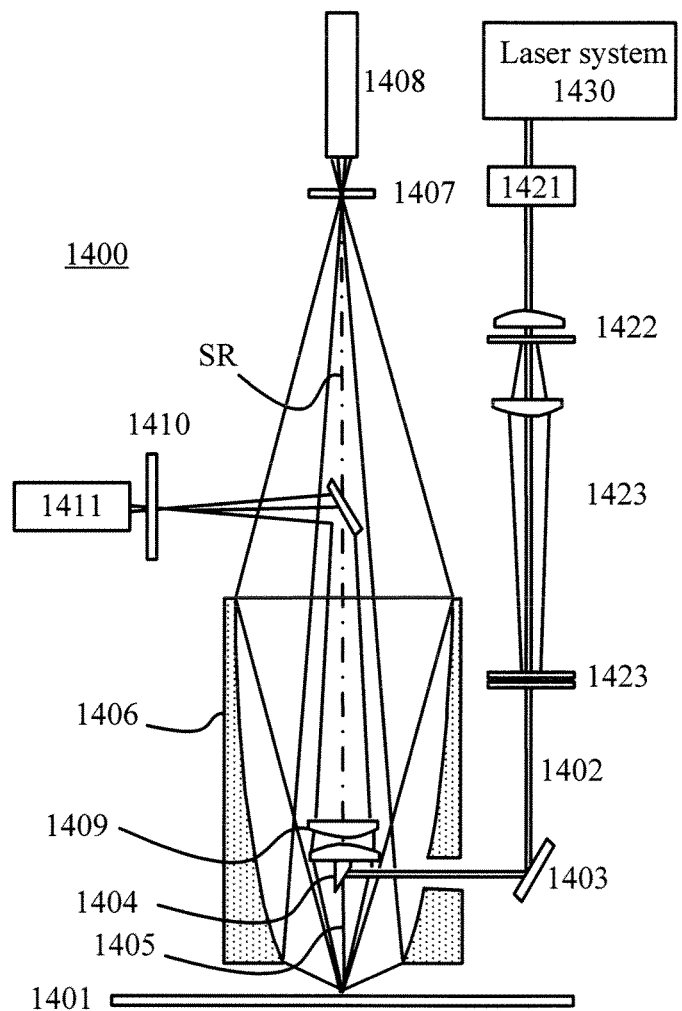
FIG. 14 illustrates a surface inspection system including one of the above-described improved illumination sources that can be used for inspecting anomalies on a surface.

FIG. 14 illustrates a surface inspection system 1400 that can be used for inspecting anomalies on a surface 1401. In this embodiment, surface 1401 can be illuminated by a substantially stationary illumination device portion of a laser system 1430 comprising a laser beam generated by the above-described illumination source. The output of laser system 1430 can be consecutively passed through polarizing optics 1421, a beam expander and aperture 1422, and beam-forming optics 1423 to expand and focus the beam.

The resulting focused laser beam 1402 is then reflected by a beam folding component 1403 and a beam deflector 1404 to direct the beam 1405 towards surface 1401 for illuminating the surface. In the preferred embodiment, beam 1405 is substantially normal or perpendicular to surface 1401, although in other embodiments beam 1405 may be at an oblique angle to surface 1401.

In one embodiment, beam 1405 is substantially perpendicular or normal to surface 1401 and beam deflector 1404 reflects the specular reflection of the beam from surface 1401 towards beam turning component 1403, thereby acting as a shield to prevent the specular reflection from reaching the detectors. The direction of the specular reflection is along line SR, which is normal to the surface 1401 of the sample. In one embodiment where beam 1405 is normal to surface 1401, this line SR coincides with the direction of illuminating beam 1405, where this common reference line or direction is referred to herein as the axis of inspection system 1400. Where beam 1405 is at an oblique angle to surface 1401, the direction of specular reflection SR would not coincide with the incoming direction of beam 1405; in such instance, the line SR indicating the direction of the surface normal is referred to as the principal axis of the collection portion of inspection system 1400.

Light scattered by small particles are collected by mirror 1406 and directed towards aperture 1407 and detector 1408. Light scattered by large particles are collected by lenses 1409 and directed towards aperture 1410 and detector 1411. Note that some large particles will scatter light that is also collected and directed to detector 1408, and similarly some small particles will scatter light that is also collected and directed to detector 1411, but such light is of relatively low intensity compared to the intensity of scattered light the respective detector is designed to detect. In one embodiment, detector 1411 can include an array of light sensitive elements, wherein each light sensitive element of the array of light sensitive elements is configured to detect a corresponding portion of a magnified image of the illumination line. In one embodiment, inspection system can be configured for use in detecting defects on unpatterned wafers. U.S. Pat. No. 6,271,916, which issued on Aug. 7, 2001 and is incorporated by reference herein, describes inspection system 1400 in further detail.

Figure 15:
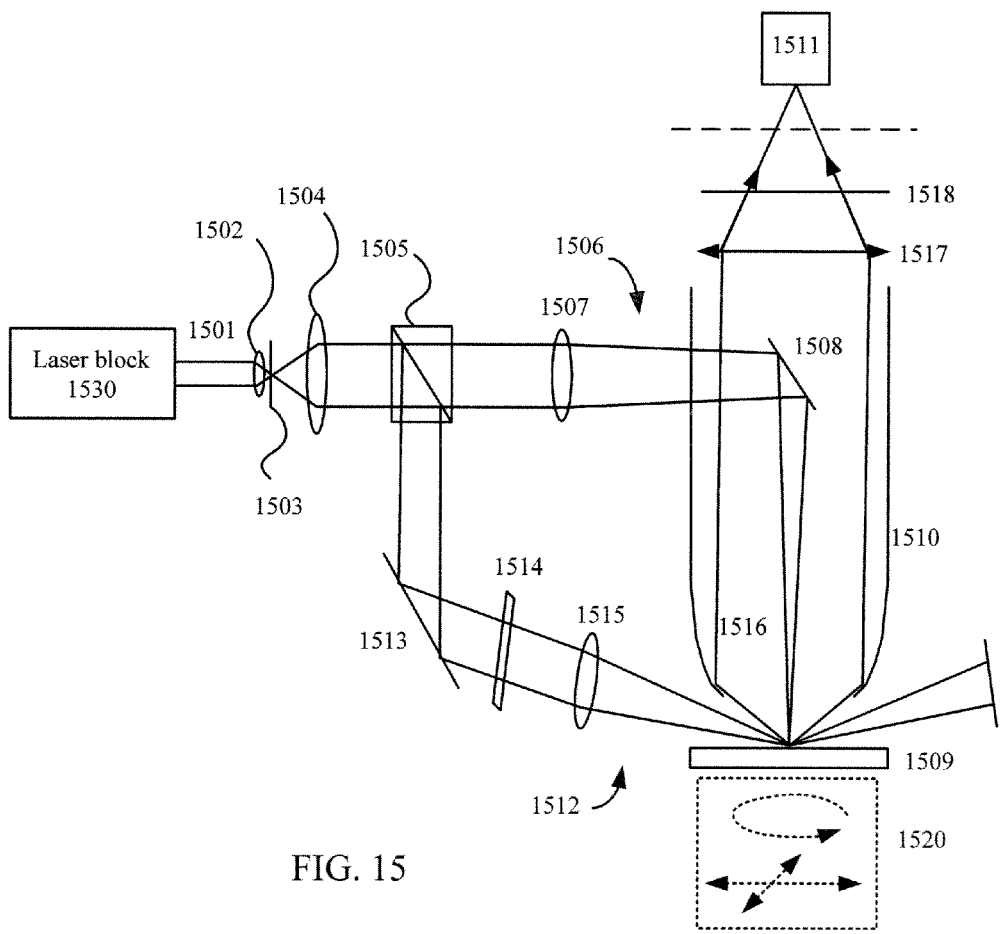
FIG. 15 illustrates an inspection system including one of the above-described improved illumination sources configured to implement anomaly detection using both normal and oblique illumination beams.

FIG. 15 illustrates an inspection system 1500 configured to implement anomaly detection using both normal and oblique illumination beams. In this configuration, a laser system 1530, which includes the above-described illumination source, can provide a laser beam 1501. A lens 1502 focuses the beam 1501 through a spatial filter 1503 and lens 1504 collimates the beam and conveys it to a polarizing beam splitter 1505. Beam splitter 1505 passes a first polarized component to the normal illumination channel and a second polarized component to the oblique illumination channel, where the first and second components are orthogonal. In the normal illumination channel 1506, the first polarized component is focused by optics 1507 and reflected by mirror 1508 towards a surface of a sample 1509. The radiation scattered by sample 1509 is collected and focused by a paraboloidal mirror 1510 to a photomultiplier tube 1511.

In the oblique illumination channel 1512, the second polarized component is reflected by beam splitter 1505 to a mirror 1513 which reflects such beam through a half-wave plate 1514 and focused by optics 1515 to sample 1509. Radiation originating from the oblique illumination beam in the oblique channel 1512 and scattered by sample 1509 is also collected by paraboloidal mirror 1510 and focused to photomultiplier tube 1511. Note that photomultiplier tube 1511 has a pinhole entrance. The pinhole and the illuminated spot (from the normal and oblique illumination channels on surface 1509) are preferably at the foci of the paraboloidal mirror 1510.

The paraboloidal mirror 1510 collimates the scattered radiation from sample 1509 into a collimated beam 1516. Collimated beam 1516 is then focused by an objective 1517 and through an analyzer 1518 to the photomultiplier tube 1511. Note that curved mirrored surfaces having shapes other than paraboloidal shapes may also be used. An instrument 1520 can provide relative motion between the beams and sample 1509 so that spots are scanned across the surface of sample 1509. U.S. Pat. No. 6,201,601, which issued on Mar. 13, 2001 and is incorporated by reference herein, describes inspection system 1500 in further detail.

Other reticle, photomask, or wafer inspection systems can advantageously use the above-described improved illumination sources. For example, other systems include those described in U.S. Pat. Nos. 5,563,702, 5,999,310, 6,201,601, 6,271,916, 7,352,457, 7,525,649, and 7,528,943. Yet further systems include those described in US Publications: 2007/0002465 and 2009/0180176. When used in an inspection system, the above-described illumination source may advantageously be combined with the coherence and speckle reducing apparatus and methods disclosed in published PCT application WO 2010/037106 and U.S. patent application Ser. No. 13/073,986. The above-described illumination source may also be advantageously combined with the methods and systems disclosed in U.S. Provisional Application 61/496,446, entitled "Optical peak power reduction of laser pulses and semiconductor and metrology systems using same", filed on Jun. 13, 2011, and in U.S. patent application Ser. No. 13/487,075, entitled "Semiconductor Inspection And Metrology System Using Laser Pulse Multiplier", filed on Jun. 1, 2012 and now published as U.S. Publication 2012/0314286 on Dec. 13, 2012. The patents, patent publications, and patent applications cited in this paragraph are incorporated by reference herein.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. Accordingly, it is intended that the scope of the invention be defined by the following claims and their equivalents.

The invention claimed is:

1. An illumination source for an inspection system, the illumination source comprising:
   a pulsed seed laser having a wavelength of approximately 1104 nm;
   a continuous wave, Raman seed laser having a wavelength of approximately 1160 nm;
   an optical coupler for combining outputs of the pulsed seed laser and the continuous wave, Raman seed laser;
   pre-amplification stages for receiving an output of the optical coupler; and
   a power amplifier for receiving an output of the pre-amplification stages,
   wherein the pre-amplification stages include a plurality of sequentially-connected pre-amplifiers.

2. The illumination source of claim 1, wherein at least one pre-amplifier uses pumped light in a direction of propagation of an input light.

3. The illumination source of claim 1, wherein at least one pre-amplifier includes an ASE filter for receiving an input from an upstream component of the illumination source, a pump laser, an optical coupler for combining outputs of the ASE filter and the pump laser, and a fiber amplifier for amplifying an output of the optical coupler.

4. The illumination source of claim 1, wherein at least one pre-amplifier uses pumped light in a direction opposite to propagation of an input light.

5. The illumination source of claim 1, wherein at least one pre-amplifier includes an ASE filter for receiving an input from an upstream component of the illumination source, a fiber amplifier for amplifying an output of the ASE filter, a pump laser, and an optical coupler for combining outputs of the fiber amplifier and the pump laser.

6. The illumination source of claim 1, wherein at least one pre-amplifier uses pumped light in a first direction opposite to propagation of an input light as well as in a second direction of the propagation.

7. The illumination source of claim 1, wherein at least one pre-amplifier includes:
   an ASE filter for receiving an input from an upstream component of the illumination source;
   a first pump laser;
   a first optical coupler for combining outputs of the ASE filter and the first pump laser;
   a fiber amplifier for amplifying an output of the first optical coupler;
   a second pump laser; and
   a second optical coupler for combining outputs of the fiber amplifier and the second pump laser.

8. An illumination source for an inspection system, the illumination source comprising:
   a pulsed seed laser having a wavelength of approximately 1104 nm;
   pre-amplification stages for receiving an output of the pulsed seed laser;
   a continuous wave, Raman seed laser having a wavelength of approximately 1160 nm;
   an optical coupler for combining outputs of the pre-amplification stages and the continuous wave, Raman seed laser; and
   a power amplifier for receiving an output of the optical coupler,
   wherein the pre-amplification stages include a plurality of sequentially-connected pre-amplifiers.

9. The illumination source of claim 8, wherein at least one pre-amplifier uses pumped light in a direction of propagation of an input light.

10. The illumination source of claim 8, wherein at least one pre-amplifier includes an ASE filter for receiving an input from an upstream component of the illumination source, a pump laser, an optical coupler for combining outputs of the ASE filter and the pump laser, and a fiber amplifier for amplifying an output of the optical coupler.

11. The illumination source of claim 8, wherein at least one pre-amplifier uses pumped light in a direction opposite to propagation of an input light.

12. The illumination source of claim 8, wherein at least one pre-amplifier includes an ASE filter for receiving an input from an upstream component of the illumination source, a fiber amplifier for amplifying an output of the ASE filter, a pump laser, and an optical coupler for combining outputs of the fiber amplifier and the pump laser.

13. The illumination source of claim 8, wherein at least one pre-amplifier uses pumped light in a first direction opposite to propagation of an input light as well as in a second direction of the propagation.

14. The illumination source of claim 8, wherein at least one pre-amplifier includes:
   an ASE filter for receiving an input from an upstream component of the illumination source;
   a first pump laser;
   a first optical coupler for combining outputs of the ASE filter and the first pump laser;
   a fiber amplifier for amplifying an output of the first optical coupler;
   a second pump laser; and
   a second optical coupler for combining outputs of the fiber amplifier and the second pump laser.

15. An illumination source for an inspection system, the illumination source comprising:
   a pulsed seed laser having a wavelength of approximately 1104 nm;
   pre-amplification stages for receiving an output of the pulsed seed laser;
   a power amplifier for amplifying an output of the pre-amplification stages;
   a continuous wave, Raman seed laser having a wavelength of approximately 1160 nm;
   an optical coupler for combining outputs of the power amplifier and the continuous wave, Raman seed laser; and
   a Raman gain fiber for receiving an output of the optical coupler,
   wherein the pre-amplification stages include a plurality of sequentially-connected pre-amplifiers.

16. The illumination source of claim 15, wherein at least one pre-amplifier uses pumped light in a direction of propagation of an input light.

17. The illumination source of claim 15, wherein at least one pre-amplifier includes an ASE filter for receiving an input from an upstream component of the illumination source, a pump laser, an optical coupler for combining outputs of the ASE filter and the pump laser, and a fiber amplifier for amplifying an output of the optical coupler.

18. The illumination source of claim 15, wherein at least one pre-amplifier uses pumped light in a direction opposite to propagation of an input light.

19. The illumination source of claim 15, wherein at least one pre-amplifier includes an ASE filter for receiving an input from an upstream component of the illumination source, a fiber amplifier for amplifying an output of the ASE filter, a pump laser, and an optical coupler for combining outputs of the fiber amplifier and the pump laser.

20. The illumination source of claim 15, wherein at least one pre-amplifier uses pumped light in a first direction opposite to propagation of an input light as well as in a second direction of the propagation.

21. The illumination source of claim 15, wherein at least one pre-amplifier includes:
   an ASE filter for receiving an input from an upstream component of the illumination source;
   a first pump laser;
   a first optical coupler for combining outputs of the ASE filter and the first pump laser;
   a fiber amplifier for amplifying an output of the first optical coupler;
   a second pump laser; and
   a second optical coupler for combining outputs of the fiber amplifier and the second pump laser.

22. A method of generating laser light of a deep UV wavelength of approximately 193 nm, the method comprising:
   generating a first wavelength of approximately 1104 nm, the first wavelength being generated by a pulsed seed laser;
   generating a second wavelength of approximately 1160 nm, the second wavelength being generated by a Raman seed laser;
   combining the first wavelength and the second wavelength to generate a combined wavelength;
   amplifying the combined wavelength; and
   generating a sixth harmonic of the combined wavelength.

23. A method of generating laser light of a deep UV wavelength of approximately 193 nm, the method comprising:
   generating a first wavelength of approximately 1104 nm, the first wavelength being generated by a pulsed seed laser;
   amplifying the first wavelength to generate a first amplified wavelength;
   generating a second wavelength of approximately 1160 nm, the second wavelength being generated by a Raman seed laser;
   combining the first amplified wavelength and the second wavelength to generate a combined wavelength;
   amplifying the combined wavelength to generate a second amplified wavelength; and
   generating a sixth harmonic of the second amplified wavelength.

24. A method of generating laser light of a deep UV wavelength of approximately 193 nm, the method comprising:
   generating a first wavelength of approximately 1104 nm, the first wavelength being generated by a pulsed seed laser;
   amplifying the first wavelength to generate a first amplified wavelength;
   generating a second wavelength of approximately 1160 nm, the second wavelength being generated by a Raman seed laser;
   combining the first amplified wavelength and the second wavelength to generate a combined wavelength;
   amplifying the combined wavelength using a Raman gain fiber to generate a second amplified wavelength; and
   generating a sixth harmonic of the second amplified wavelength.

25. A system for inspecting a specimen such as a reticle, photomask or wafer, said system comprising:
   an illumination source including:
   a pulsed seed laser having a wavelength of approximately 1104 nm;
   a continuous wave, Raman seed laser having a wavelength of approximately 1160 nm;
   an optical coupler for combining outputs of the pulsed seed laser and the continuous wave, Raman seed laser;
   pre-amplification stages for receiving an output of the optical coupler; and
   a power amplifier for receiving an output of the pre-amplification stages,
   wherein the pre-amplification stages include a plurality of sequentially-connected pre-amplifiers.

26. A system for inspecting a specimen such as a reticle, photomask or wafer, said system comprising:
   an illumination source including:
   a pulsed seed laser having a wavelength of approximately 1104 nm;
   pre-amplification stages for receiving an output of the pulsed seed laser;
   a continuous wave, Raman seed laser having a wavelength of approximately 1160 nm;
   an optical coupler for combining outputs of the pre-amplification stages and the continuous wave, Raman seed laser; and
   a power amplifier for receiving an output of the optical coupler,
   wherein the pre-amplification stages include a plurality of sequentially-connected pre-amplifiers.

27. A system for inspecting a specimen such as a reticle, photomask or wafer, said system comprising:
   an illumination source including:
   a pulsed seed laser having a wavelength of approximately 1104 nm;
   pre-amplification stages for receiving an output of the pulsed seed laser;
   a power amplifier for amplifying an output of the pre-amplification stages;
   a continuous wave, Raman seed laser having a wavelength of approximately 1160 nm;
   an optical coupler for combining outputs of the power amplifier and the continuous wave, Raman seed laser; and
   a Raman gain fiber for receiving an output of the optical coupler,
   wherein the pre-amplification stages include a plurality of sequentially-connected pre-amplifiers.

28. A method of inspecting a reticle, photomask, or wafer, the method comprising:
   generating a wavelength of approximately 1104 nm;
   amplifying said approximately 1104 nm wavelength with one or more stages of fiber amplification;
   generating a wavelength of approximately 1160 nm;
   amplifying said approximately 1160 nm wavelength with a fiber Raman amplifier, wherein said Raman amplifier is pumped with said amplified wavelength of approximately 1104 nm, and wherein the generated 1160 nm wavelength is combined with the 1104 nm light before a final stage of amplification;
   generating a sixth harmonic of the approximately 1160 nm wavelength after it has been amplified by the Raman amplifier; and
   illuminating the reticle, photomask, or wafer being inspected with sixth harmonic light.

* * * * *